(12) United States Patent
Aono et al.

(10) Patent No.: US 7,385,758 B2
(45) Date of Patent: Jun. 10, 2008

(54) TOTAL INTERNAL REFLECTION FLUORESCENCE MICROSCOPE

(75) Inventors: Yasushi Aono, Yokohama (JP); Tsuyoshi Mochizuki, Hachioji (JP); Kazuhiko Osa, Hachioji (JP)

(73) Assignee: Olympus Corporation, Tokyo (JP)

( * ) Notice: Subject to any disclaimer, the term of this patent is extended or adjusted under 35 U.S.C. 154(b) by 62 days.

(21) Appl. No.: 10/816,489

(22) Filed: Mar. 31, 2004

(65) Prior Publication Data
US 2004/0196457 A1 Oct. 7, 2004

(30) Foreign Application Priority Data
Apr. 4, 2003 (JP) ............... 2003-101346

(51) Int. Cl.
*G02B 21/06* (2006.01)
(52) U.S. Cl. ............... 359/390; 359/368; 359/385
(58) Field of Classification Search ............... 359/368, 359/385, 390
See application file for complete search history.

(56) References Cited

U.S. PATENT DOCUMENTS 4,972,258 A * 11/1990 Wolf et al. ............... 348/79
5,866,911 A * 2/1999 Baer ............... 250/458.1
6,055,097 A * 4/2000 Lanni et al. ............... 359/386
2003/0086163 A1* 5/2003 Aono et al. ............... 359/388

FOREIGN PATENT DOCUMENTS

JP 3093145 B2 7/2000
JP 2001-013413 A 1/2001

OTHER PUBLICATIONS

D. Axelrod, 5. Total Internal Reflection Fluorescence at Biological Surfaces, *Noninvasive Techniques in Cell Biology*, pp. 93-127 (1990).

* cited by examiner

Primary Examiner—Joshua L Pritchett
(74) Attorney, Agent, or Firm—Frishauf, Holtz, Goodman & Chick, P.C.

(57) ABSTRACT

A condenser lens is disposed in a position facing an objective lens via a specimen, a reflection mirror is movably disposed in the vicinity of an outermost part of a transmitted illuminative light path on the side of a transmitted illuminative light source from the condenser lens, and a laser beam output from a laser oscillation unit is reflected by the reflection mirror and is incident upon the condenser lens.

42 Claims, 13 Drawing Sheets

TOTAL INTERNAL REFLECTION FLUORESCENCE MICROSCOPE

CROSS-REFERENCE TO RELATED APPLICATIONS

This application is based upon and claims the benefit of priority from prior Japanese Patent Application No. 2003-101346, filed Apr. 4, 2003, the entire contents of which are incorporated herein by reference.

BACKGROUND OF THE INVENTION

1. Field of the Invention

The present invention relates to a total internal reflection fluorescence microscope for performing fluorescence observation by use of an evanescent light generated by total internal reflection illumination.

2. Description of the Related Art

In recent years, a total internal reflection fluorescence microscopy (hereinafter referred to as TIRFM) has attracted attentions as a microscope for fluorescence observation of a living thing. In this TIRFM, an illuminative light is totally reflected by a boundary surface between a cover glass and a specimen, and a fluorescent substance is excited using a light called an evanescent light which leaks into a small region having a size of several hundreds nm or less on a specimen side. In this TIRFM, only the fluorescence of the small region in the vicinity of the cover glass is observed. An observed image of TIRFM provides a very dark background. Accordingly, it is possible to observe fluorescence having a high contrast and faint fluorescence.

Additionally, in a site of biological research using TIRFM, there are a case where a shallow plane is to be observed with good contrast in the vicinity of the boundary surface between the cover glass and the specimen, and a case where the evanescent light is extended to a certain degree of depth to observe a broad range. Therefore, it is desirable to change a leak-out depth of the evanescent light in accordance with the specimen.

The leak-out depth of the evanescent light from the boundary surface is described, for example, in D. Axelrod's document "Total Internal Reflection Fluorescence at Biological Surfaces". Accordingly, the following equation is established.

$$d = \lambda / 4\pi \sqrt{(n_1^2 \cdot \sin\theta_1^2 - n_2^2)} \quad (1),$$

where d denotes the leak-out depth of the evanescent light, $\lambda$ denotes a wavelength of the light, $n_1$ denotes a refractive index on the incidence side, $\theta_1$ denotes an incidence angle, and $n_2$ denotes a refractive index on an emission side.

Therefore, when the incidence angle $\theta_1$ of the illuminative light with respect to the boundary surface, that is, an inclination angle of the illuminative light with respect to a normal to the boundary surface increases, the leak-out depth d of the evanescent light becomes shallow. In actual TIRFM, a laser beam having a high coherent property is used, and the incidence angle of the illuminative light is adjusted. Accordingly, the incidence angle of the laser beam onto the boundary surface changes, and the leak-out depth of the evanescent light is adjusted.

FIGS. 17A to 17C are diagrams showing a function of TIRFM described in Jpn. Pat. No. 3093145. An objective lens 1 has a numerical aperture with which total internal reflection illumination is possible. A specimen 3 is laid on a cover glass 2. A mirror 4 is movable in a direction crossing an optical axis direction of the objective lens 1 at right angles.

A laser beam 5 for use as the illuminative light is incident upon the mirror 4. In this state, as shown in FIGS. 17A to 17C, the mirror 4 moves in the direction crossing the optical axis direction of the objective lens 1 at right angles. Accordingly, an incidence position of the laser beam incident upon the objective lens 1 moves in a direction distant from an optical axis of the objective lens 1. By the movement of the incidence position of the laser beam, the incidence angle of the laser beam 5 emitted toward the boundary surface between the cover glass 2 and the specimen 3 from the objective lens 1 changes. The laser beam 5 emitted from the objective lens 1 is totally reflected by the boundary surface between the cover glass 2 and specimen 3 via an immersion oil 6 as shown in FIG. 17C.

FIG. 18 is a constitution diagram of TIRFM described in Jpn. Pat. Appln. KOKAI Publication No. 2001-013413. The TIRFM includes a laser illuminating device 7 which outputs the laser beam 5. In the TIRFM, the laser beam 5 is incident upon a side surface 10 of a point ball lens 9 of a condenser lens for transmission illuminating 8 and the total internal reflection illumination is possible. The laser illuminating device 7 is rotatable with respect to a microscope main body 11. The laser illuminating device 7 rotates centering on an intersection of the boundary surface of the cover glass 2 and specimen 3 and the observation optical axis. Accordingly, the laser beam 5 changes its incidence angle with respect to the boundary surface between the cover glass 2 and specimen 3.

Additionally, the incidence angle of the laser beam 5 needs to be inclined by a critical angle or more, at which the total internal reflection occurs. Here, assuming that a refractive index on a cover glass 2 side via the boundary surface between the cover glass 2 and specimen 3 is $n_1$, and a refractive index on a specimen 3 side is $n_2$, a critical angle $\theta c$ is represented by the following equation (2).

$$\sin \theta c = n_2 / n_1 \quad (2)$$

Therefore, conditions of the incidence angle $\theta_1$ for realizing the total internal reflection illumination is represented by the following equation (3).

$$n_1 \cdot \sin \theta_1 > n_2 \quad (3)$$

On the other hand, to incline an incident light of the laser beam 5 passing through the objective lens 1 as in the Jpn. Pat. No. 3093145 shown in FIGS. 17A to 17C, a maximum incidence angle $\theta$max that can be set depends on the numerical aperture (NA) of the objective lens 1, and is represented by the following equation (4).

$$n_1 \cdot \sin \theta\text{max} = NA \quad (4)$$

Therefore, for the conditions for realizing the total internal reflection illumination, the NA of the objective lens 1 needs to be larger than the refractive index $n_2$.

In general, a refractive index of a living cell is about 1.37 to 1.38. The NA of the objective lens 1 for use needs to be about 1.4 at minimum.

At present, a magnification of the objective lens having an NA of 1.4 or more is limited to a high magnification of 60 times or more. To realize a high NA by the objective lens 1 having a low magnification, an effective diameter of the objective lens 1 needs to be increased. However, it is difficult to increase the effective diameter of the objective lens 1 while keeping a standard diameter of an attaching screw of the objective lens 1. Therefore, in the TIRFM shown in FIGS. 17A to 17C, total internal reflection fluorescence observation at a magnification of about 20 or 40 times is impossible.

In the TIRFM shown in FIG. 18, when the laser beam 5 is incident from a condenser lens for transmission illuminating 8 side, an illuminative range can be set without depending on the objective lens 1. Accordingly, the total internal reflection fluorescence observation using the objective lens 1 having a low magnification is possible.

However, in the TIRFM shown in FIG. 18, the laser illuminating device 7 is disposed right beside the point ball lens 9 of the condenser lens for transmission illuminating 8. Additionally, the laser illuminating device 7 itself needs to be rotated. Therefore, a considerable space is necessary including a holding section of a rotary mechanism and a space of a track of the rotating laser illuminating device 7. Consequently, a space in which the specimen 3 is laid is compressed. It is supposed that operation properties are remarkably impaired.

An irradiation range of the laser beam is set in such a manner that an observation range of the objective lens 1 having the low magnification can be illuminated. Then, in the observation with the objective lens 1 having the high magnification, only a part of the irradiation range of the laser beam is observed. Therefore, the laser beam with which another part is irradiated is useless.

An energy density of the laser beam on the surface of the specimen 3 is in inverse proportion to an irradiation area. In the observation with the objective lens 1 having the high magnification, the irradiation range of the laser beam is condensed so as to illuminate only a range required for the observation, and the energy density of the laser beam is preferably enhanced.

Especially, there is an experiment for the purpose of detection of very weak fluorescence such as a single molecule. In this experiment, the irradiation energy density of the laser beam is required to be as high as possible. On the other hand, in the TIRFM, the leak-out depth of the evanescent light is changeable. In recent years, the TIRFM has been spread in the site of the biological research. Furthermore, there has started to be a demand for the simultaneous illuminating of a plurality of optional wavelengths in optional depths.

This background has the following actual circumstances. Improvement of fluorescent protein such as GFP has been advanced, and it becomes easy to observe a dynamic state or a function of the living cell with multicolored fluorescence. Moreover, as seen also from Axelrod formula (equation (1)), the leak-out depth of the evanescent light depends also on the wavelength of the light. Therefore, there is a principle problem that a range to be observed differs, when the wavelength differs even at the equal laser beam incidence angle. There is also a realistic problem that a depth position of a tissue in a cell corresponding to each wavelength differs.

In the TIRFM, it is possible to switch the incidence angle or the wavelength of the laser beam at a high speed using mechanical means or electric driving means such as a motor. However, in cases where a simultaneous property in a strict meaning is required such as a case where a fast phenomenon is traced, there is a restriction on a high-speed switch. In this case, it is necessary to simultaneously-illuminate introductory portions of the laser beams disposed in a plurality of places.

However, in the TIRFM shown in FIG. 17A, a dichroic mirror is used in order to reflect the laser beam on a objective lens 1 side and to transmit the fluorescence on an observation side.

Additionally, when there are a plurality of wavelengths to be illuminated, the dichroic mirror needs to have wavelength characteristics of the corresponding multi-band. The dichroic mirror of the multi-band has a high difficulty in manufacturing, and is expensive. Furthermore, the dichroic mirror of the multi band has a bad separation level of the wavelength, and brightness and SN ratio of a fluorescent image are deteriorated. When the illuminative wavelengths are to be further increased halfway, the dichroic mirror needs to be newly prepared again.

On the other hand, to prevent the dichroic mirror from being used, as shown in FIG. 19, it is possible to dispose a total internal reflection mirror 12 in a position of an outermost portion of a pupil of the objective lens 1. However, it is necessary to dispose another total internal reflection mirror 13 also in the outermost portion of the pupil of the objective lens 1 on an opposite side in order to prevent the laser beam 5 totally reflected by the boundary surface between the cover glass and the specimen 3 from passing on an observation side.

Therefore, a considerable part of the pupil of the objective lens 1, which should have been originally used 100% for observation, is lost by the respective total internal reflection mirrors 12, 13. Therefore, a capability of the objective lens 1 is deteriorated.

In the TIRFM shown in FIG. 18, as described above, the laser illuminating device 7 is disposed right beside the point ball lens 9 of the condenser lens for transmission illuminating 8, and additionally the laser illuminating device 7 itself needs to be rotated. Therefore, a considerable space is required including the space of the track of the holding section of the rotation mechanism or the rotating laser illuminating device 7. In this constitution, when the laser illuminating device 7 including an emission angle adjustment section of independent laser beams is to be disposed, two laser illuminating devices at maximum can be disposed on opposite sides of the condenser lens for transmission illuminating 8.

Moreover, each TIRFM has a common problem. There is a case where a plurality of wavelengths are observed by the use of the evanescent lights having different depths. For example, when a shallow region is observed with B excitation, and a deep region is observed with G excitation, the B and G excitations can be simultaneously observed only in the shallow region. In this case, the image of the G excitation can only be observed as a defocused background image. Therefore, for example, the whole cell film is dyed by a fluorescent reagent, and the image of the TIRFM in the deep region can be used only in limited applications such as grasping of an approximate size of the cell.

While the objective lens is fixed, the surfaces in the different depths can be simultaneously observed. Then, the application of multi-wavelength TIRFM can further be broadened to simultaneous observation of forms of small organs in the vicinity of the cell film and inside the cell.

BRIEF SUMMARY OF THE INVENTION

According to a major aspect of the present invention, there is provided a total internal reflection fluorescence microscope comprising: at least one objective lens which takes light from a specimen; an image pick-up device which picks up an image of the light taken into the objective lens; an observation optical path via which the light taken into the objective lens is condensed onto the image pick-up device; a condenser lens which is disposed in a position facing the objective lens via the specimen and which has a numerical aperture making possible total internal reflection illumination and which guides a transmitted illuminative light into the specimen; and a laser introduction section which allows a laser beam to be incident upon a direction crossing the optical path of the transmitted illuminative light at right angles and which introduces the incident laser beam on a condenser lens side in the vicinity of an outermost part of the transmitted illuminative light path.

DETAILED DESCRIPTION OF THE INVENTION

A first embodiment of the present invention will be described hereinafter with reference to the drawings.

Figure 1:
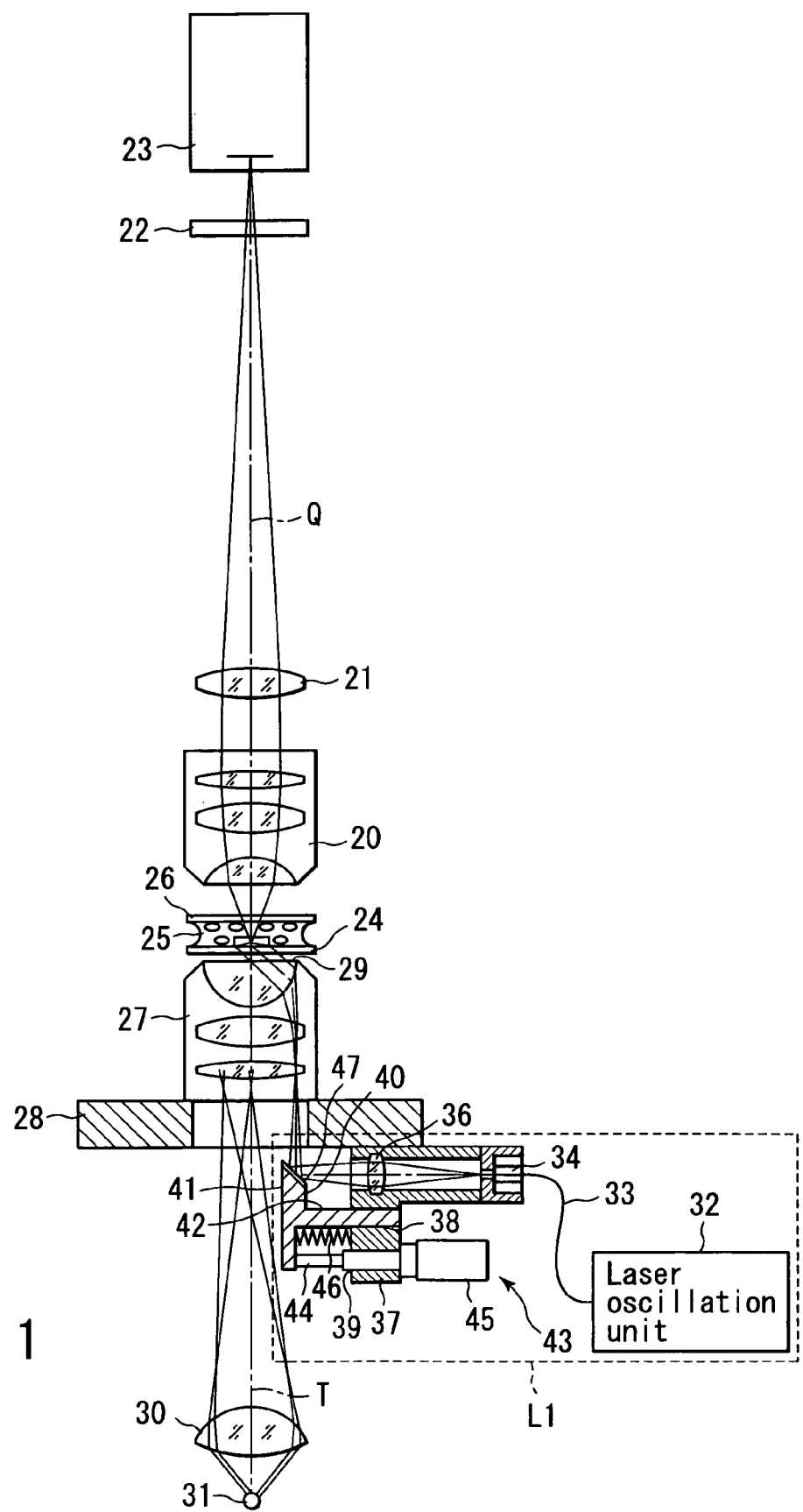
FIG. 1 is a constitution diagram showing a first embodiment of TIRFM according to the present invention.

FIG. 1 is a constitution diagram of an erected type total internal reflection fluorescence microscopy (TIRFM). An image forming lens 21, emission filter 22, and image pick-up device 23 are disposed on an observation optical path Q of an objective lens 20. The emission filter 22 is a band pass filter which passes a light only of a specific wavelength band $\lambda_{E1}$ longer than a wavelength $\lambda_{L1}$ of a laser beam output from a laser oscillation unit 32 described later. The image pick-up device 23 is disposed in a focal position of the image forming lens 21.

A slide glass for observation 24 is disposed under the objective lens 20. A specimen 25 is placed on the slide glass 24. The specimen 25 is covered with a cover glass 26.

A condenser lens 27 is disposed in a position facing the objective lens 20 via the slide glass 24. The condenser lens 27 is disposed on a base 28. An immersion oil 29 is dotted/attached to a tip of the condenser lens 27. Accordingly, the immersion oil 29 is charged between the condenser lens 27 and slide glass 24.

A numerical aperture (NA) of the condenser lens 27 is designed to be larger than a refractive index of the specimen 25. That is, assuming that a refractive index of the immersion oil 29 or the slide glass 24 is $n_1$, and a refractive index of the specimen 25 is $n_2$, the following relation is established from above equations (3) and (4):

$$NA = n_1 \cdot \sin \theta_{max} > n_2 \qquad (5),$$

where $\theta_{max}$ corresponds to a maximum incidence angle at which the incidence is possible through the immersion oil 29 and slide glass 24 from the condenser lens 27.

In general, the refractive index of the living cell is about 1.37 to 1.38. Accordingly, the numerical aperture of the condenser lens 27 has a value larger than the refractive index of the living cell of 1.37 to 1.38, and concretely has a value of about 1.65 to 1.45.

A collector lens 30 and transmitted illuminative light source 31 are disposed on a transmitted illuminative light path T of the condenser lens 27. The collector lens 30 introduces the illuminative light output from the transmitted illuminative light source 31 into the condenser lens 27.

A laser introduction section $L_1$ is disposed under a base 28. The laser introduction section $L_1$ includes the laser oscillation unit 32. For example, a laser diode is used in the laser oscillation unit 32. An oscillation wavelength of the laser oscillation unit 32 has a single wavelength $\lambda_{L1}$.

A laser output end of the laser oscillation unit 32 is connected to an optical fiber 33. One end of the optical fiber 33 is preferably a single mode fiber. A fiber emission end 34 is disposed on the other end of the optical fiber 33. The fiber emission end 34 emits the laser beam transmitted through the optical fiber 33 as a divergent ray. The fiber emission end 34 is connected, for example, to one end of a support section 35 having a hollow structure.

The support section 35 is fixed/supported, for example, on the bottom surface of the base 28. A condensing lens 36 converts a divergent ray emitted from the fiber emission end 34 into a convergent ray, and condenses the light in the vicinity of a front focal position of the condenser lens 27.

A downward support portion 37 is disposed integrally with a lower part of the support section 35. A hole for movement 38 and a hole for support 39 are disposed in the downward support portion 37. The hole for movement 38 and hole for support 39 are disposed in a direction substantially crossing the transmitted illuminative light path T at right angles.

A mirror holding section 40 is movably disposed in the hole for movement 38. For the mirror holding section 40, a mirror support section 41 and a movement guide section 42 are integrally formed. The movement guide section 42 is inserted in the hole for movement 38, and is movable in the hole for movement 38. The mirror support section 41 is disposed substantially in a direction crossing the movement guide section 42 at right angles.

A micrometer 43 is disposed in the hole for support 39. The micrometer 43 includes a micrometer head 44 and a micrometer operation section 45. The micrometer head 44 abuts on the lower part of the mirror support section 41. The micrometer operation section 45 directly moves the micrometer head 44 by rotation. A translatory direction of the micrometer head 44 agrees with the direction crossing the transmitted illuminative light path T substantially at right angles.

A spring 46 is disposed between the mirror support section 41 and the downward support portion 37. The spring 46 has a tensile force to urge the mirror support section 41 on a micrometer head 44 side. Accordingly, the micrometer head 44 abuts on and is kept by the mirror support section 41.

A reflective mirror 47 is disposed on an upper end of the mirror support section 41. Therefore, when the micrometer operation section 45 is rotated, the micrometer head 44 moves in a translatory manner in a direction crossing the transmitted illuminative light path T substantially at right angles. In response to this movement, the mirror support section 41 moves in the translatory manner in the direction crossing the transmitted illuminative light path T substantially at right angles. As a result, the reflective mirror 47 moves in the translatory manner in the direction crossing the transmitted illuminative light path T substantially at right angles. It is to be noted that the mirror holding section 40, micrometer 43, and spring 46 constitute a mirror movement section.

The reflective mirror 47 is disposed in the vicinity of an outermost side of the opening diameter of the condenser lens 27. The reflective mirror 47 reflects upwards the laser beam introduced from the direction crossing the transmitted illuminative light path T substantially at right angles upwards substantially at right angles.

Next, an operation of the TIRFM constituted as described above will be described.

The laser oscillation unit 32 oscillates the laser beam having a wavelength $\lambda_{L1}$ The laser beam having the wavelength $\lambda_{L1}$ is introduced into the optical fiber 33, and emitted as a divergent ray from the fiber emission end 34. The laser beam emitted as the divergent ray is converted to the convergent ray through the condensing lens 36 and is incident upon the reflective mirror 47.

The laser beam incident upon the reflective mirror 47 is reflected on the condenser lens 27 side in the vicinity of the outermost side of the transmitted illuminative light path T. The laser beam reflected by the reflective mirror 47 is once condensed in the vicinity of the front focal position of the condenser lens 27 by the condensing lens 36. Moreover, the laser beam is incident upon the condenser lens 27, and is emitted as a parallel ray advancing in an oblique direction from the condenser lens 27. The laser beam emitted from the condenser lens 27 is transmitted through the immersion oil 6 and is incident upon the boundary surface between the slide glass 24 and the specimen 25.

When the incidence angle $\theta_{L1}$ of the laser beam upon the boundary surface between the slide glass 24 and the specimen 25 is larger than the critical angle of the total internal reflection, the laser beam is totally reflected by the boundary surface. Accordingly, the evanescent light leaks on a specimen 25 side.

The specific fluorescent substance existing in the specimen 25 is excited by the evanescent light having the wavelength $\lambda_{L1}$ By this excitation, the fluorescent substance emits the fluorescence such that a maximum luminance wavelength of the fluorescence is in a transmission wavelength band $\lambda_{E1}$ of the emission filter 22. The fluorescence is incident upon the objective lens 20 through the cover glass 26. Furthermore, the fluorescence is transmitted through the emission filter 22, and is incident upon the image pick-up device 23. The image pick-up device 23 picks up a fluorescent image of the wavelength band $\lambda_{E1}$.

On the other hand, when the micrometer operation section 45 is rotated, the reflective mirror 47 moves in the translatory manner in the direction crossing the transmitted illuminative light path T at right angles. When the position of the reflective mirror 47 moves in the direction crossing the transmitted illuminative light path T substantially at right angles, the incidence position of the laser beam upon the condenser lens 27 moves. Accordingly, an emission angle of the laser beam emitted from the condenser lens 27, that is, an incidence angle $\theta_{L1}$ of the laser beam upon the boundary surface between the slide glass 24 and specimen 25 changes.

The leak-out depth of the evanescent light in the total internal reflection illumination changes with the incidence angle $\theta_{L1}$ of the laser beam upon the boundary surface between the slide glass 24 and specimen 25. Therefore, the micrometer operation section 45 is rotated to slightly move the reflective mirror 47 in the direction crossing the transmitted illuminative light path T-substantially at right angles. That is when the reflective mirror 47 is brought close to or far from the transmitted illuminative light path T, the leak-out depth $d_{L1}$ of the evanescent light can be optionally changed.

It is to be noted that when the transmission illuminating observation is performed using the illuminative light output from the transmitted illuminative light source 31, the reflective mirror 47 is completely retreated from the transmitted illuminative light path T.

As described above, according to the first embodiment, the condenser lens 27 is disposed in the position facing the objective lens 20 via the specimen 25, the reflective mirror 47 is movably disposed in the vicinity of the outermost part of the transmitted illuminative light path T on the transmitted illuminative light source 31 side from the condenser lens 27, and the laser beam output from the laser oscillation unit 32 is reflected by the reflective mirror 47 and is incident upon the condenser lens 27. That is, the laser beam which excites the fluorescent substance dyed by the specimen 25 is not transmitted through the objective lens 20, and is transmitted through the condenser lens 27 positioned so as to face the objective lens 20.

Accordingly, a maximum incidence angle θmax of the laser beam incident upon the boundary-surface between the slide glass 24 and the specimen 25 depends only on the NA of the condenser lens 27 represented by the above equation (5). Therefore, fluorescence observation by the total internal reflection illumination is possible regardless of the NA or the magnification of the objective lens 20.

The laser introduction section $L_1$ is disposed apart from the specimen 25 and the condenser lens 27. Accordingly, there is not any structure disposed in the vicinity of the specimen 25, and a space in the vicinity of the specimen 25 is not compressed.

The laser introduction section $L_1$ includes a structure in which the reflective mirror 47 is moved by the micrometer 43. The laser introduction section $L_1$ has a simple structure and also has a narrow operation range. Therefore, for the laser introduction section $L_1$, the TIRFM itself can be compact, and the TIRFM can have a superior operation property.

The first embodiment may also be modified as follows.

A glass bottom dish may also be used in the slide glass 24. Accordingly, the cover glass 26 may also be omitted. In this case, when an operating distance of the objective lens 20 is short, an immersion objective lens is used in the objective lens 20.

For example, an electromotive motor, piezo-actuator or the like may also be used in the micrometer 43 for moving the reflective mirror 47.

The reflective mirror 47 is fixed. The fiber emission end 34 and condensing lens 36 are integrally moved in a direction parallel to the transmitted illuminative light path T. Even with this constitution, a function similar to that of the first embodiment is obtained. In this case, the fiber emission end 34 and condensing lens 36 are moved, for example, using a micro-motor, electromotive motor, piezo-actuator, or the like.

The first embodiment is applicable not only to the erected type but also to an inverted microscope.

An optical observation system is not limited to the constitution by the image forming lens 21, emission filter 22, and image pick-up device 23, and can be optionally constituted as long as the fluorescence wavelength with respect to the excited wavelength of the laser introduction section $L_1$ is selected and the image can be picked up.

In the first embodiment, the laser beam emitted from the fiber emission end 34 is converted to the convergent ray by the single condensing lens 36, and the convergent ray is reflected by the reflective mirror 47 and condensed in the vicinity of the front focal position of the condenser lens 27. The present invention is not limited to this. For example, the laser beam emitted from the fiber emission end 34 is converted to a parallel light flux by a single lens or a plurality of lenses, the condensing lens is disposed in an optional position on the optical path from when the parallel light flux is reflected by the reflective mirror 47 and is incident upon the vicinity of the front focal position of the condenser lens 27, and the light may be condensed by the condensing lens.

A second embodiment of the present invention will be described with reference to the drawings. It is to be noted that the same part as that of FIG. 1 is denoted with the same reference numerals and detailed description thereof is omitted.

Figure 2:
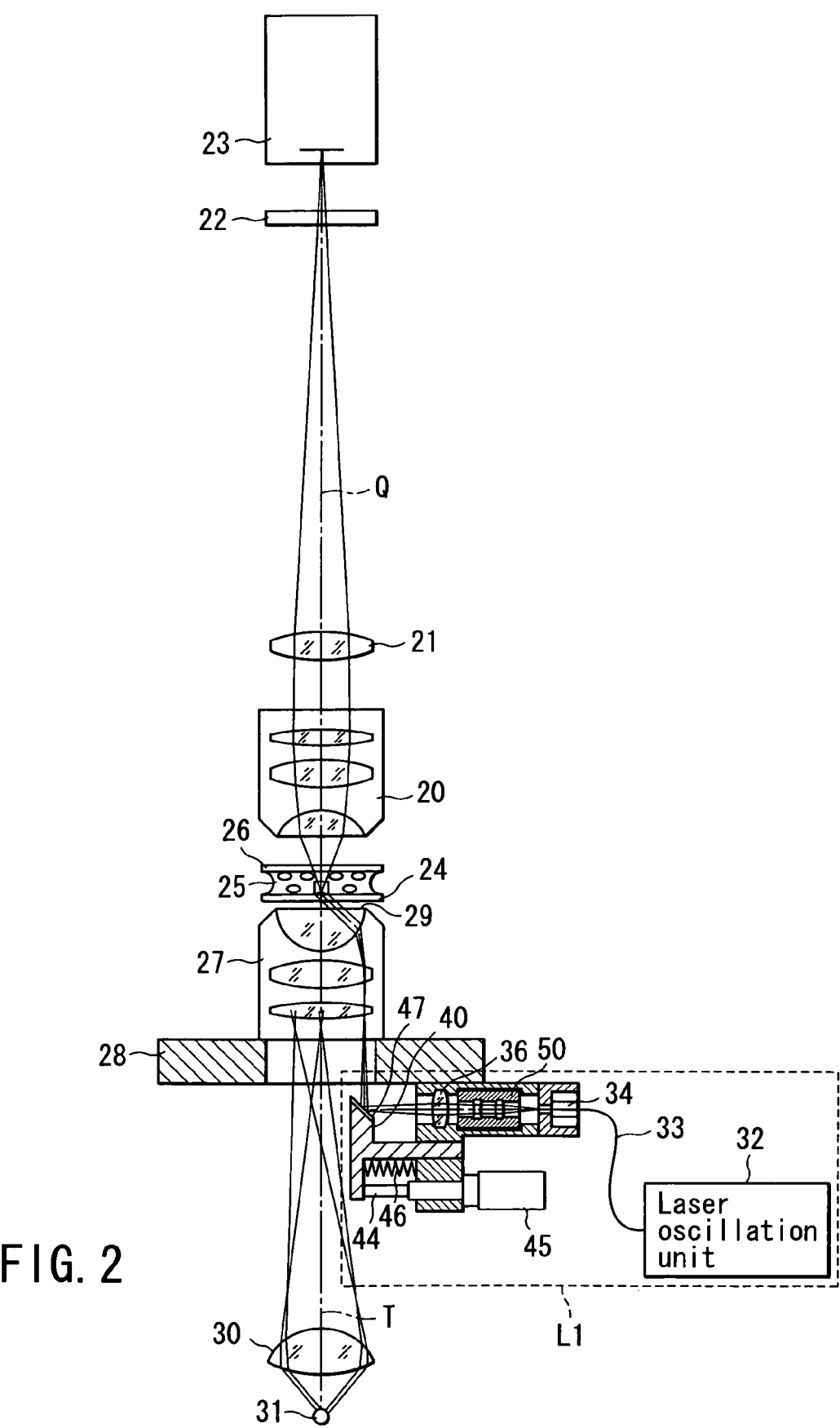
FIG. 2 is a constitution diagram showing a second embodiment of the TIRFM of the present invention.

FIG. 2 is a constitution diagram showing the erected type total internal reflection fluorescence microscopy (TIRFM). A conversion lens unit 50 is disposed between the fiber emission end 34 and the condensing lens 36. The conversion lens unit 50 is integrally detachably inserted with respect to a laser introductory optical path between the fiber emission end 34 and the condensing lens 36.

Figure 3:
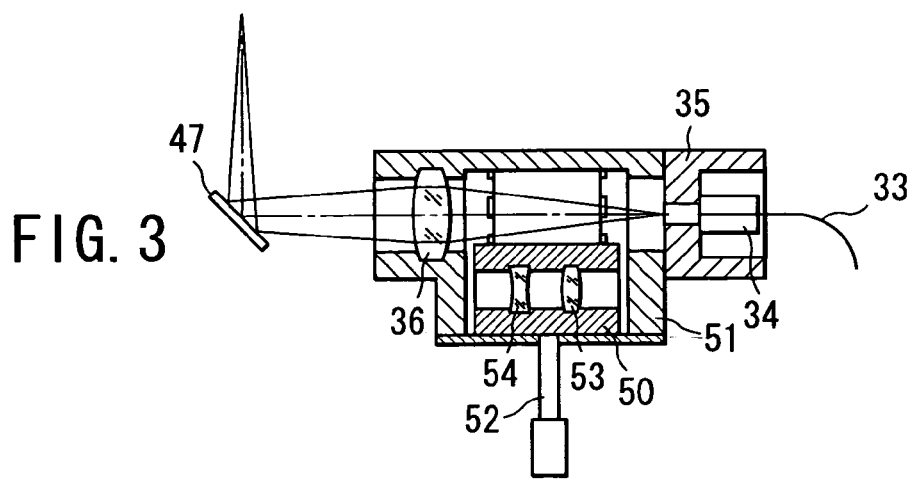
FIG. 3 is an enlarged top plan view of a conversion lens unit in the TIRFM.
Figure 4:
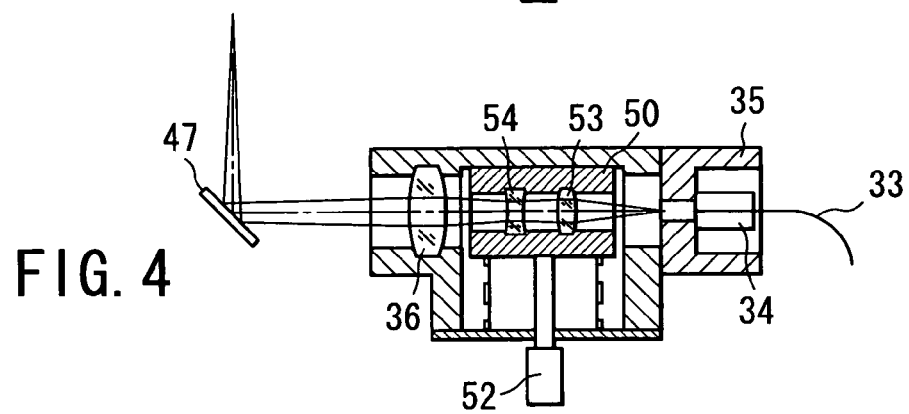
FIG. 4 is an enlarged top plan view of the conversion lens unit in the TIRFM.

FIGS. 3 and 4 are enlarged top plan views of the conversion lens unit 50. A shelter space portion 51 is disposed in the side surface of the support section 35 including a hollow structure. The conversion lens unit 50 is provided with a knob 52. The knob 52 protrudes out of the shelter space portion 51 through the wall of the shelter space portion 51. The conversion lens unit 50 is detachably inserted between the laser introductory optical path in the support section 35 and the inside of the shelter space portion 51 by the operation of the knob 52. For example, when the knob 52 is pulled out as shown in FIG. 3, the conversion lens unit 50 comes out of the laser introductory optical path. When the knob 52 is pushed in as shown in FIG. 4, the conversion lens unit 50 is inserted into the laser introductory optical path.

The conversion lens unit 50 has, for example, a hollow structure. A convex lens 53 and concave lens 54 are disposed in the conversion lens unit 50. The convex lens 53 converts the NA of a divergent laser beam emitted from the fiber emission end 34.

The concave lens 54 is disposed movably in an optical axis direction of the laser introductory optical path between the convex lens 53 and condensing lens 36. The concave lens 54 diverges the laser beam NA-converted by the convex lens 53. Accordingly, when the concave lens 54 is moved in the optical axis direction of the laser introductory optical path, the laser beam can be condensed in the vicinity of the front focal position of the condenser lens 27 through the condensing lens 36. Therefore, the focal distance of the condensing lens 36 is adjustable by the concave lens 54.

Next, the operation of the TIRFM constituted as described above will be described.

When the knob 52 is pushed inwards as shown in FIG. 4, the conversion lens unit 50 is inserted into the laser introductory optical path. The NA of the laser beam diverged from the fiber emission end 34 is converted by the convex lens 53 in this state.

Thereafter, the laser beam is condensed in the vicinity of the front focal position of the condenser lens 27 through the concave lens 54 and condensing lens 36 At this time, the incidence NA of the laser beam upon the condenser lens 27 is reduced as compared with a case where the convex lens 53 and concave lens 54 deviate from the laser introductory optical path. Accordingly, the laser beam is condensed in the vicinity of the front focal position of the condenser lens 27 at a small incidence NA.

As a result, a ray flux diameter of the parallel ray advancing in an oblique direction after passing through the condenser lens 27, that is, a laser beam irradiation range in the specimen 25 is condensed. Accordingly, energy density of the laser beam increases.

As described above, according to the second embodiment, the conversion lens unit 50 including the convex lens 53 and concave lens 54 is detachably attached onto the laser introductory optical path. Accordingly, the irradiation range of the laser beam on the specimen 25 can be condensed. That is, the energy density of the laser beam with which the specimen 25 is irradiated can be converted, for example, to be high.

Therefore, when the weak fluorescence is to be observed with a strong power, the conversion lens unit 50 is inserted into the laser introductory optical path. In the fluorescence observation of the broad range, the conversion lens unit 50 is detached from the laser introductory optical path. The specimen 25 is selectively used in accordance with the application of the observation in this manner.

The second embodiment may also be modified as follows.

Inserting/detaching means of the conversion lens unit 50 is not limited to the knob and may also be, for example, the electromotive motor and can be freely constituted.

The conversion lens unit 50 is not limited to a combination of the convex lens 53 and concave lens 54, and may also be a combination of the convex and concave lenses, from which the same function is obtained.

For the conversion lens unit 50, one type of unit is constituted to be detachably inserted between the fiber emission end 34 and condensing lens 36, but the present invention is not limited to this. For example, the conversion lens unit 50 is converted to a different incidence NA, and is selectively detachably inserted between the fiber emission end 34 and condensing lens 36. With the constitution, the specimen 25 can be irradiated with the laser beams having three or more different incidence NA. Accordingly, a finer irradiation range of the laser beam, and further the energy density are adjustable.

A third embodiment of the present invention will be described with reference to the drawing. It is to be noted that the same part as that of FIG. 2 is denoted with the same reference numerals, and detailed description is omitted.

Figure 5:
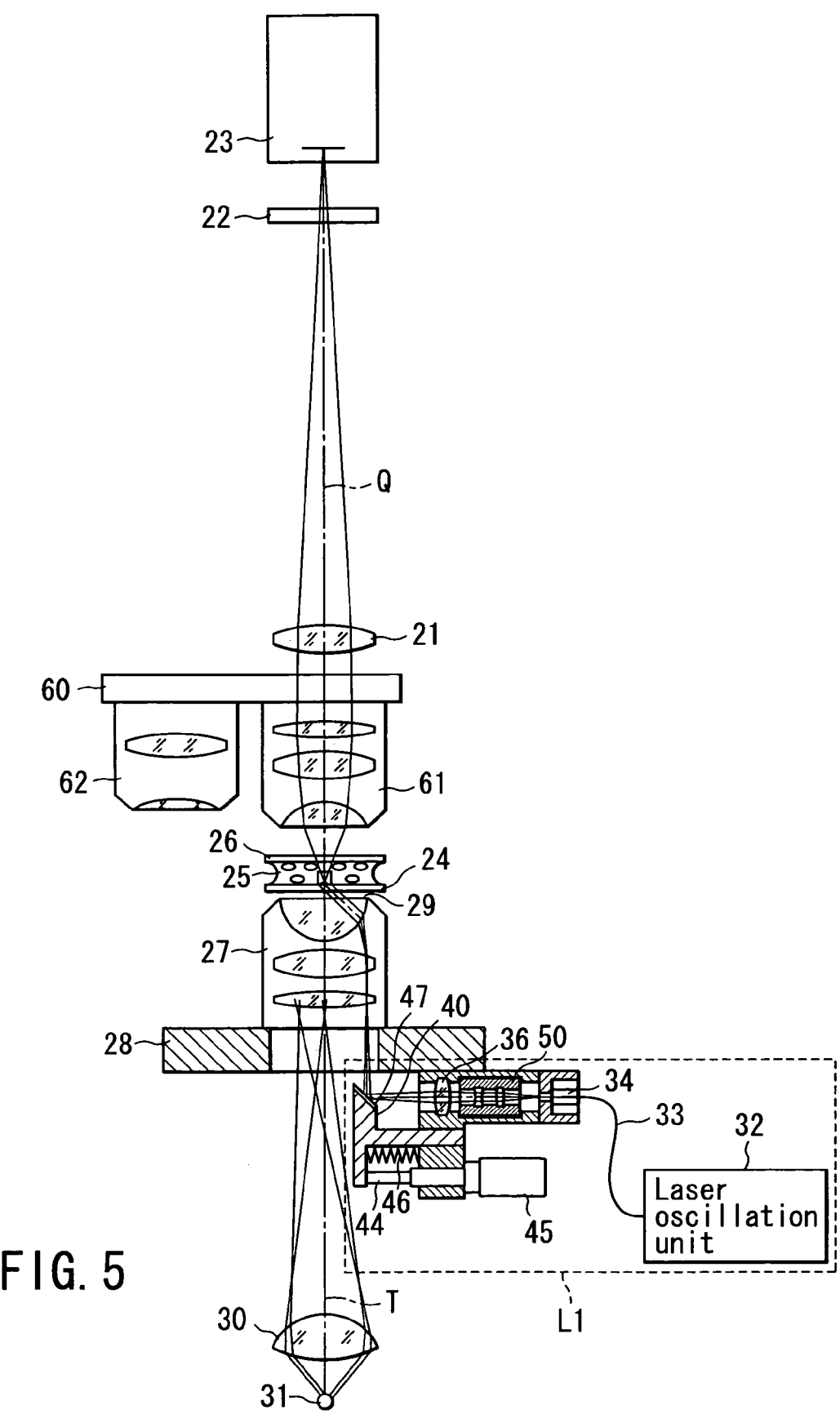
FIG. 5 is a constitution diagram showing a third embodiment of the TIRFM of the present invention.

FIG. 5 is a constitution diagram of the erected type total internal reflection fluorescence microscopy (TIRFM). An objective lens for high-magnification observation 61 and an objective lens for low-magnification observation 62 are attached to an objective lens switching section 60.

Figure 6:
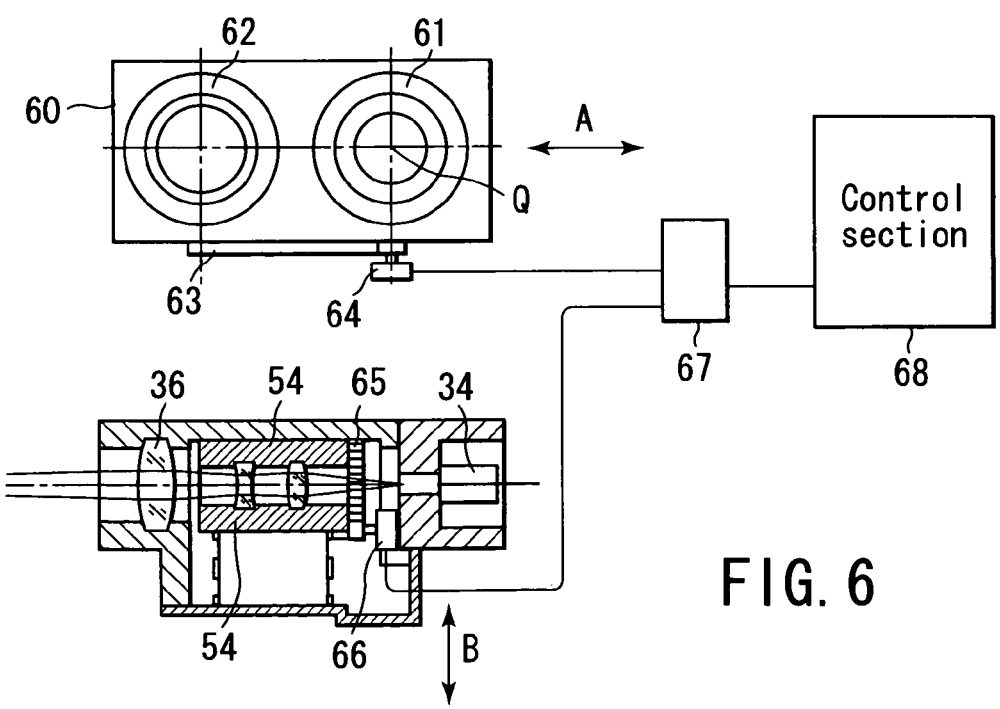
FIG. 6 is a diagram showing each objective lens switch mechanism in the TIRFM.

FIG. 6 is a diagram showing a switch mechanism for the respective objective lenses 61, 62. A member for switching 63, such as a rack, is disposed on the side surface of the objective lens switching section 60. The member for switching 63 is connected to a magnification switch driving section 64 via a pinion or the like. When the magnification switch driving section 64 is rotated/driven, this rotation driving is transmitted to the member for switching 63, and converted to a translatory movement in an arrow A direction. Accordingly, the objective lens switching section 60 moves in the arrow A direction, and the objective lens for high-magnification observation 61 or the objective lens for low-magnification observation 62 is disposed on the observation optical path Q.

A member for inserting/detaching 65, such as the rack, is disposed on the end surface of the conversion lens unit 50 on the incidence side. The member for inserting/detaching 65 is connected to an inserting/detaching driving section 66 such as the electromotive motor via a pinion or the like. When the inserting/detaching driving section 66 is rotated/driven, the rotating/driving is transmitted to the member for inserting/detaching 65 and converted to the translatory movement in an arrow B direction. Accordingly, the conversion lens unit 50 moves in the arrow B direction, and is detachably inserted with respect to the laser introductory optical path.

The laser beam irradiation range is set so as to substantially agree with an observation range of the objective lens for high-magnification observation 61 in a state in which the conversion lens unit 50 is inserted into the laser introductory optical path. The laser beam irradiation range is set so as to substantially agree with the observation range of the objective lens for low-magnification observation 62 in a state in which the conversion lens unit 50 is detached from the laser introductory optical path.

The magnification switch driving section 64 and inserting/detaching driving section 66 is connected to a control section 68 via a driver 67. The driver 67 receives a driving command transmitted from the control section 68 to drive the magnification switch driving section 64 and inserting/detaching driving section 66.

The control section 68 includes a personal computer and the like. The control section 68 executes switching program, and transmits a driving command to the driver 67 to insert the conversion lens unit 50 in the laser introductory optical path, when the objective lens for high-magnification observation 61 is disposed on the observation optical path Q. The control section 68 executes the switching program, and transmits a driving command to the driver 67 to detach the conversion lens unit 50 from the laser introductory optical path, when the objective lens for low-magnification observation 62 is disposed on the observation optical path Q.

Next, the operation of the TIRFM constituted as described above will be described.

When the objective lens for high-magnification observation 61 is disposed on the observation optical path Q, the conversion lens unit 50 is inserted into the laser introductory optical path. Accordingly, the laser beam irradiation range with respect to the specimen 25 substantially agrees with the observation range of the objective lens for high-magnification observation 61.

When the objective lens for low-magnification observation 62 is inserted into the observation optical path Q, the conversion lens unit 50 deviates from the laser introductory optical path. Accordingly, the laser beam irradiation range with respect to the specimen 25 substantially agrees with the observation range of the objective lens for low-magnification observation 62.

Therefore, according to the third embodiment, when the objective lens for high-magnification observation 61 or objective lens for low-magnification observation 62 is switched to switch the observation magnification, the laser beam irradiation range can also be switched so as to substantially agree with a size of visual field for the observation of the specimen 25.

It is to be noted that the third embodiment may also be modified as follows.

Three or more objective lenses having different magnifications may also be used. In this case, a plurality of conversion lens units having different reduction ratios of the respective laser beam irradiation range are disposed corresponding to a plurality of objective lenses. The control section 68 inserts the corresponding conversion lens unit into the laser introductory optical path in cooperation with the switching of each objective lens.

When the cooperation of the switching of the respective objective lenses with the inserting/detaching of the conversion lens unit with respect to the laser introductory optical path is not required, the switching of the respective objective lenses and the inserting/detaching of the conversion lens unit may be independently switched. In this case, the switching of the respective objective lenses and the inserting/detaching of the conversion lens unit may also be performed manually.

A fourth embodiment of the present invention will be described with reference to the drawings.

Figure 7A:
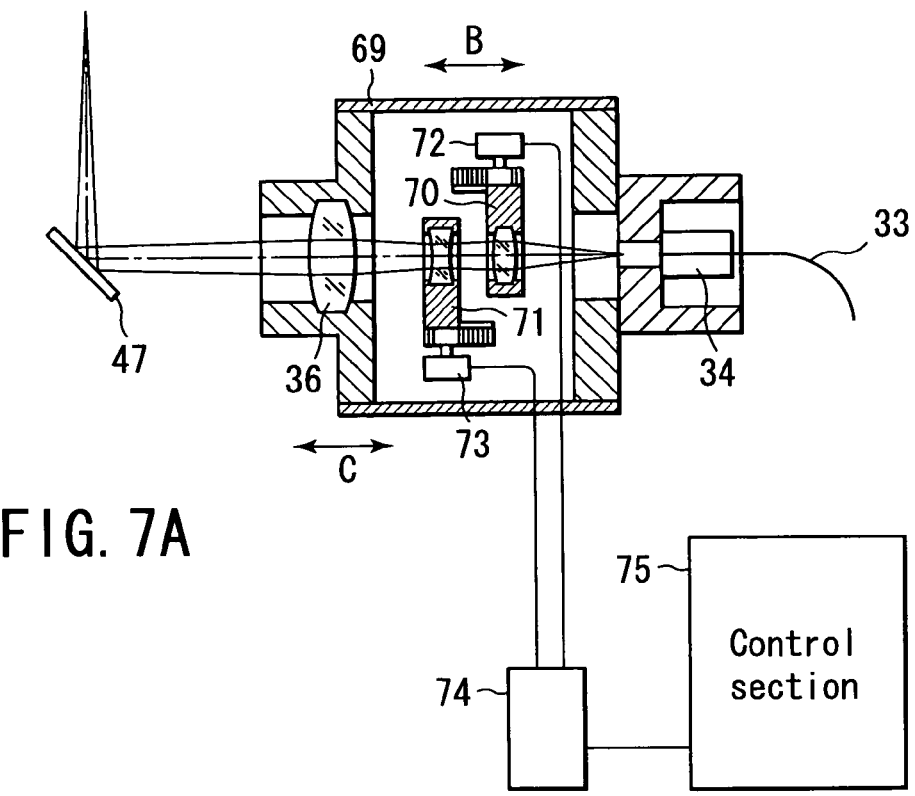
FIG. 7A is a constitution diagram showing the conversion lens unit in a fourth embodiment of the TIRFM of the present invention.
Figure 7B:
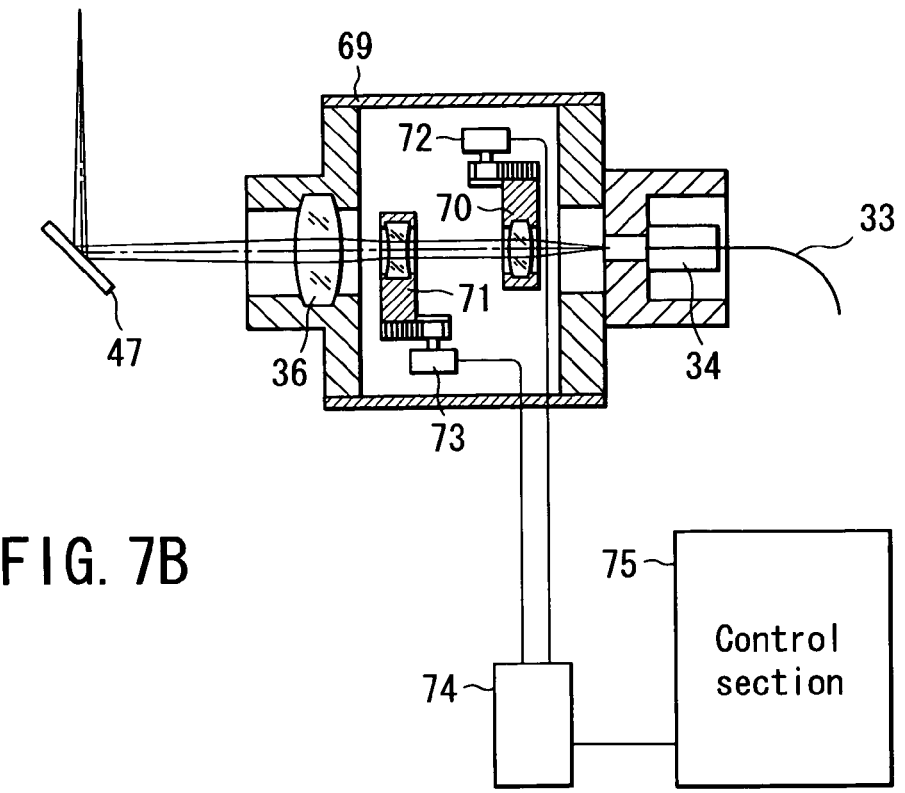
FIG. 7B is a diagram showing an operation of the conversion lens unit.

FIGS. 7A and 7B are constitution diagrams showing a zoom lens unit 69 in the total internal reflection fluorescence microscopy (TIRFM). A convex lens 70 and concave lens 71 are disposed in the zoom lens unit 69. The convex lens 70 is disposed movably in the optical axis direction of the laser introductory optical path between the fiber emission end 34 and the condensing lens 36. The convex lens 70 converts the NA of the divergent laser beam emitted from the fiber emission end 34.

The concave lens 71 is disposed movably in the optical axis direction of the laser introductory optical path-between the convex lens 70 and the condensing lens 36. The concave lens 71 diverges the laser beam whose NA is converted by the convex lens 70. Accordingly, when the concave lens 71 is moved in the optical axis direction of the laser introductory optical path, the laser beam can be condensed in the vicinity of the front focal position of the condenser lens 27 through the condensing lens 36. Therefore, by the concave lens 71, the focal distance of the condensing lens 36 is adjustable.

The convex lens 70 is provided with a moving section 72. The moving section 72 moves the convex lens 70 in the optical axis direction (arrow B direction) of the laser introductory optical path. The moving section 72 includes, for example, the electromotive motor and the like.

The concave lens 71 is provided with a moving section 73. The moving section 72 moves the concave lens 71 in the optical axis direction (arrow C direction) of the laser introductory optical path. The moving section 73 includes, for example, the electromotive motor and the like.

The respective moving sections 72, 73 is connected to a control section 75 via a driver 74. The driver 74 receives the driving command emitted from the control section 75 to drive the respective moving sections 72, 73.

The control section 75 includes the personal computer and the like. The control section 75 executes driving program to determine a moving position of the concave lens 71 for adjusting the condensing position of the laser beam in the vicinity of the front focal position of the condenser lens 27 in accordance with the positional movement of the convex lens 70. The control section 75 controls a moving/driving amount of the respective moving sections 72, 73 based on the information of the determined moving position of the concave lens 71.

Next, the operation of the TIRFM constituted as described above will be described.

The control section 75 executes the driving program to emit the driving command to the driver 74. The driver 74 receives the driving command emitted from the control section 75 to drive the respective moving sections 72, 73. Accordingly, the moving section 72 moves the convex lens 70 in the optical axis direction (arrow B direction) of the laser introductory optical path as shown in FIGS. 7A and 7B. The moving section 73 moves the concave lens 71 in the optical axis direction (arrow C direction) of the laser introductory optical path as shown in FIGS. 7A and 7B.

At this time, the control section 75 determines the moving position of the concave lens 71 for adjusting the condensing position of the laser beam in the vicinity of the front focal position of the condenser lens 27 in accordance with the positional movement of the convex lens 70, and controls the moving/driving amounts of the respective moving sections 72, 73 based on the information of the determined moving position of the concave lens 71.

Accordingly, the NA of the divergent laser beam emitted from the fiber emission end 34 is converted by the convex lens 70 whose position is moved. The focal distance of the laser beam whose NA has been converted is adjusted by passage through the concave lens 71 and condensing lens 36. As a result, the laser beam is condensed in the vicinity of the front focal position of the condenser lens 27.

Therefore, only the incidence NA can be continuously converted without changing the condensing position of the laser beam. As a result, the ray flux diameter of the parallel ray advancing in the oblique direction after passing through the condenser lens 27, that is, the size of the laser beam irradiation range in the specimen 25 is continuously converted. The energy density of the laser beam is continuously converted in accordance with the change of the laser beam irradiation range.

As described above, according to the fourth embodiment, the convex lens 70 and concave lens 71 in the zoom lens unit 69 are disposed movably in the optical axis direction of the laser introductory optical path. Accordingly, the laser beam irradiation range in the specimen 25, that is, the energy density of the laser beam can be continuously converted. When the weak fluorescence is to be detected with a strong power, the laser beam irradiation range is condensed. For the fluorescence observation in the broad range, the laser beam irradiation range is enlarged. In this manner, it is possible to selectively use the specimen 25 in accordance with the applications such as the observation purpose.

It is to be noted that the fourth embodiment may also be modified as follows.

Figure 8:
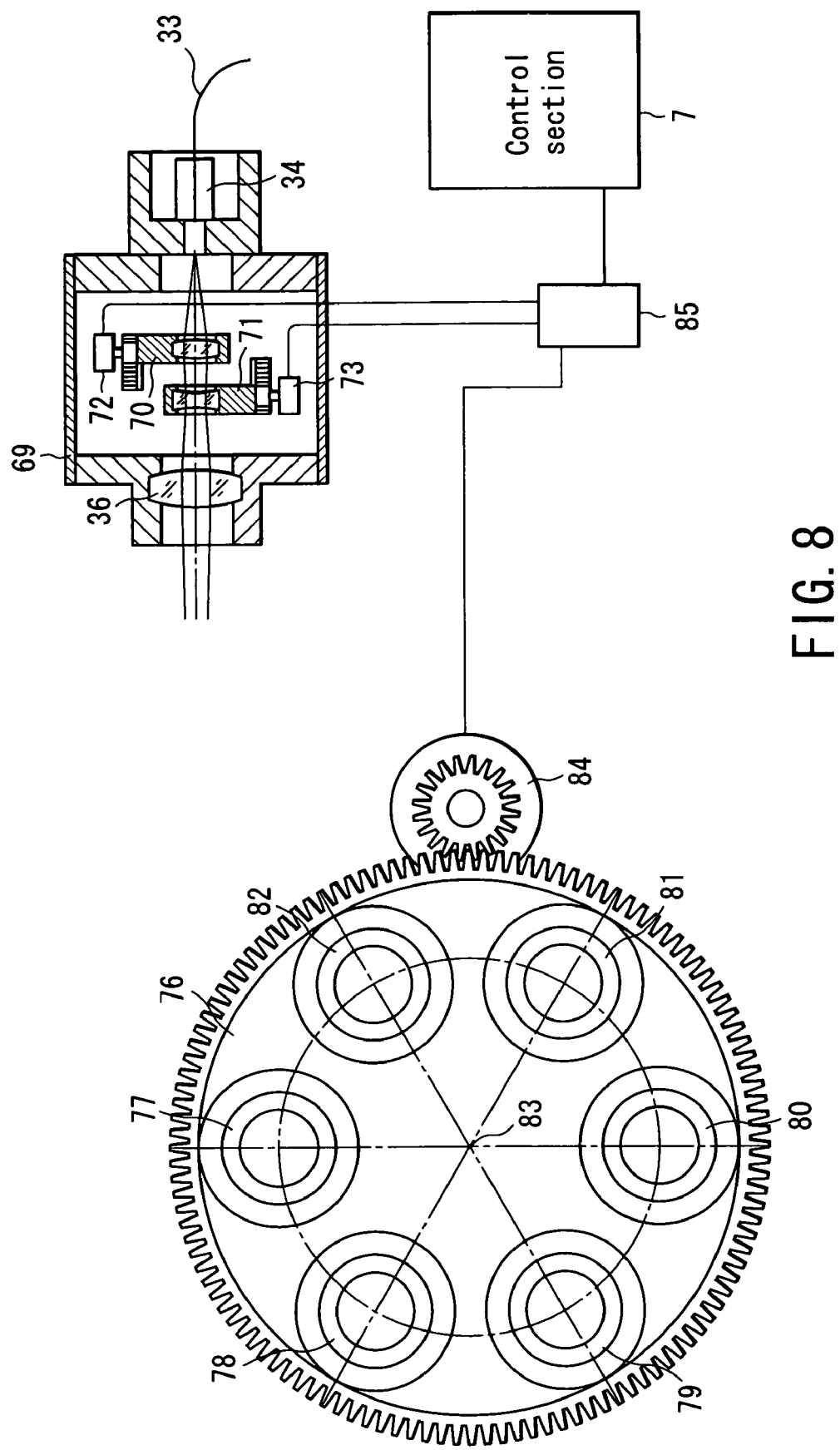
FIG. 8 is a constitution diagram showing a modification of the fourth embodiment of the present invention.

FIG. 8 is a constitution diagram of the modification. It is to be noted that the same parts as those of FIGS. 7A and 7B are denoted with the same reference numerals, and the detailed description is omitted. An objective lens revolver (objective lens switching section) 76 is provided with a plurality of objective lenses 77 to 82 having different observation magnifications. The objective lens revolver 76 rotates centering on a rotation axis 83, and any one is selected from the respective objective lenses 77 to 82 and disposed on the observation optical path Q.

An observation magnification switching section 84 rotates the objective lens revolver 76 and selects any one from the objective lenses 77 to 82 to set the objective lens on the observation optical path Q. The observation magnification switching section 84 includes, for example, the electromotive motor and the like.

The observation magnification switching section 84 is connected to the control section 75 via a driver 85. The driver 74 receives the driving command emitted from the control section 75 to drive the observation magnification switching section 84.

The control section 75 executes the driving program to emit the switching command to the observation magnification switching section 84 to select the observation magnification of the objective lenses 77 to 82. Moreover, the control section 75 determines the respective positions of the convex lens 70 and concave lens 71 so as to obtain the laser beam irradiation range which substantially agrees with the observation range in the observation magnifications of the objective lenses 77 to 82, and emits the driving command to the observation magnification switching section 84 based on the determined positional information.

With this constitution, when the objective lenses 77 to 82 having optional observation magnifications are selected, the laser beam irradiation range substantially agreeing with the observation range of the objective lens can be switched/set in cooperation with the selected objective lens.

The zoom lens unit 69 is not limited to the combination of the convex lens 70 and concave lens 71, and may be a combination of the convex and concave lenses, from which the same function is obtained.

A fifth embodiment of the present invention will be described with reference to the drawing. It is to be noted that the same part as that of FIG. 1 is denoted with the same reference numerals and the detailed description thereof is omitted.

Figure 9:
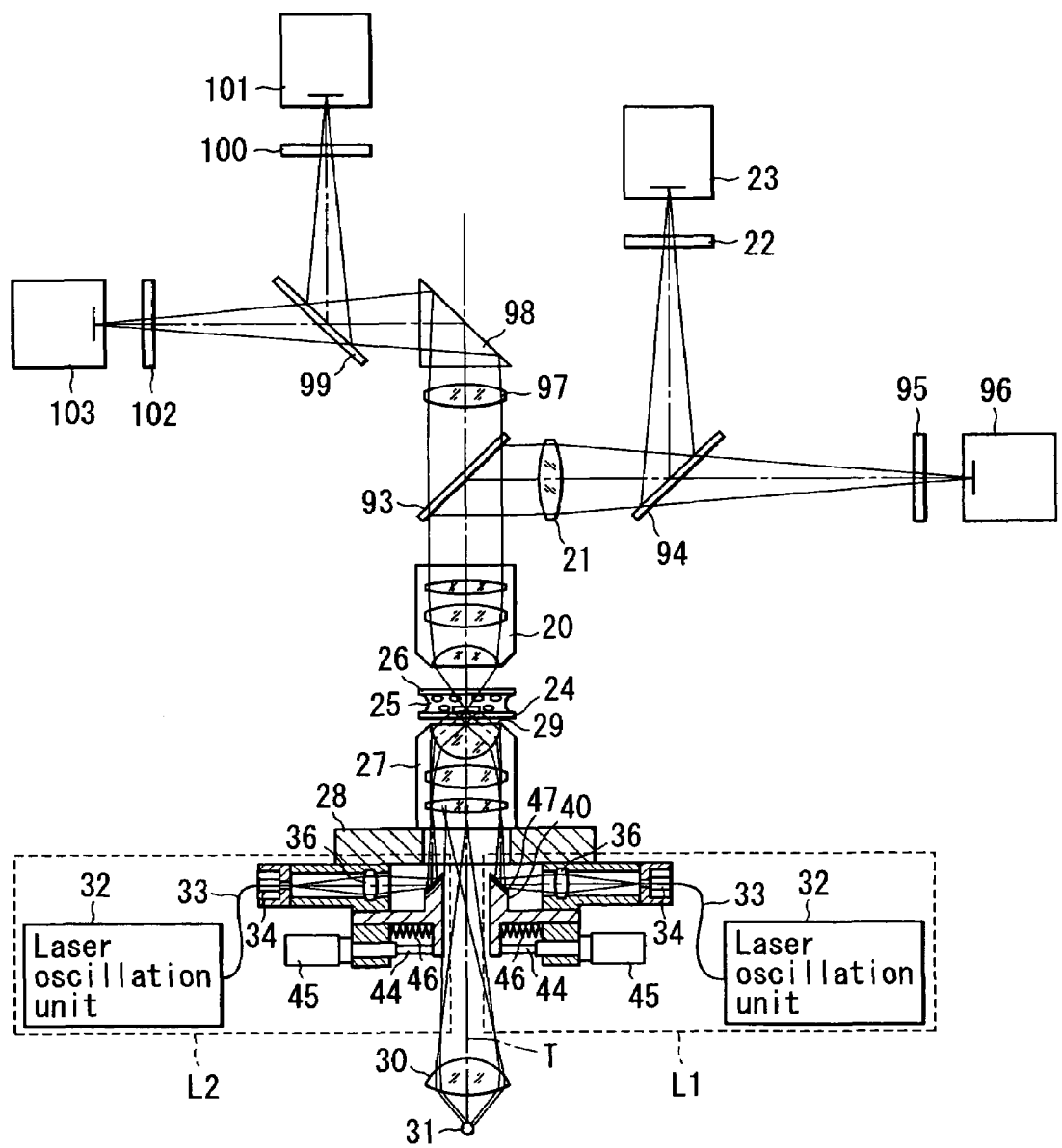
FIG. 9 is a constitution diagram showing a fifth embodiment of the TIRFM of the present invention.

FIG. 9 is a constitution diagram of the erected type total internal reflection fluorescence microscopy (TIRFM). In a lower part of the base 28, for example, four laser introduction sections (hereinafter referred to as first to fourth laser introduction sections) $L_1$, $L_2$, $L_3$, $L_4$ are disposed in the lower part of the base 28. The first to fourth laser introduction sections $L_1$, $L_2$, $L_3$, $L_4$ are disposed every equal angle centering on the transmitted illuminative light path T. That is, the first to fourth laser introduction sections $L_1$, $L_2$, $L_3$, $L_4$ are radially disposed in the direction crossing the transmitted illuminative light path T substantially at right angles. The first and second laser introduction sections $L_1$, $L_2$ are disposed facing each other via the transmitted illuminative light path T. The third and fourth laser introduction sections $L_3$, $L_4$ are disposed facing each other via the transmitted illuminative light path T. Since the second to fourth laser introduction sections $L_2$, $L_3$, $L_4$ have the same constitution as that of the first laser introduction section $L_1$, the detailed description of the constitution is omitted.

Additionally, the respective wavelengths of the laser beams emitted from the first to fourth laser introduction sections $L_1$, $L_2$, $L_3$, $L_4$ are different from one another. The first laser introduction section $L_1$ outputs the laser beam having a single wavelength $\lambda_{L1}$. The second laser introduction section $L_2$ outputs the laser beam having a single wavelength $\lambda_{L2}$. The third laser introduction section $L_3$ outputs the laser beam having a single wavelength $\lambda_{L3}$. The fourth laser introduction section $L_4$ outputs the laser beam having a single wavelength $\lambda_{L4}$.

Next, the constitution on an observation optical path Q side will be described. A first dichroic mirror 93 is disposed on the observation optical path Q. The first dichroic mirror 93 has characteristics that the mirror reflects the light having a wavelength shorter than a standard wavelength $\lambda_1$ and transmits the light having a wavelength longer than the wavelength $\lambda_1$.

The image forming lens 21 and a second dichroic mirror 94 are disposed on a reflective optical path of the first dichroic mirror 93. The second dichroic mirror 94 has a wavelength $\lambda_2$ which is a standard wavelength shorter than the wavelength $\lambda_1$, and has characteristics that the mirror reflects the light on the side of the wavelength shorter than the wavelength $\lambda_2$ and transmits the light on the long wavelength side.

The first emission filter 22 and first image pick-up device 25 are disposed on the reflective optical path of the second dichroic mirror 94. The first emission filter 22 is a band pass filter which transmits only the light having a specific wavelength band $\lambda_{E1}$ shorter than the wavelength $\lambda_2$. The first image pick-up device 25 is disposed in the focal position of the first image forming lens 21.

A second emission filter 95 and second image pick-up device 96 are disposed on the transmission optical path of the second dichroic mirror 94. The second emission filter 95 is a band pass filter which transmits the light only of a specific wavelength band $\lambda_{E2}$ between the wavelengths $\lambda_{L2}$ and $\lambda_{L1}$. The second image pick-up device 96 is disposed in the focal position of the first image forming lens 21.

On the other hand, a second image forming lens 97 and a total internal reflection prism 98 are disposed on the transmission optical path of the first dichroic mirror 93. A third dichroic mirror 99 is disposed on the reflective optical path of the total internal reflection prism 98.

The third dichroic mirror 99 has a wavelength $\lambda_3$ which is a standard wavelength shorter than the wavelength $\lambda_1$, and has characteristics that the mirror reflects the light on the side of the wavelength shorter than the wavelength $\lambda_3$ and transmits the light on the long wavelength side. A third emission filter 100 and a third image pick-up device 101 are disposed on the reflective optical path of the third dichroic mirror 99. The third emission filter 100 is a band pass filter which transmits the light only of a specific wavelength band $\lambda_{E3}$ between the wavelengths $\lambda_1$ and $\lambda_3$. The third image pick-up device 101 is disposed in the focal position of the second image forming lens 97.

A fourth emission filter 102 and fourth image pick-up device 103 are disposed on the transmission optical path of the third dichroic mirror 99. The fourth emission filter 102 is a band pass filter which transmits the light only of a specific wavelength band $\lambda_{E4}$ longer than the wavelength $\lambda_{L3}$. The fourth image pick-up device 103 is disposed in the focal position of the second image forming lens 97.

Figure 11:
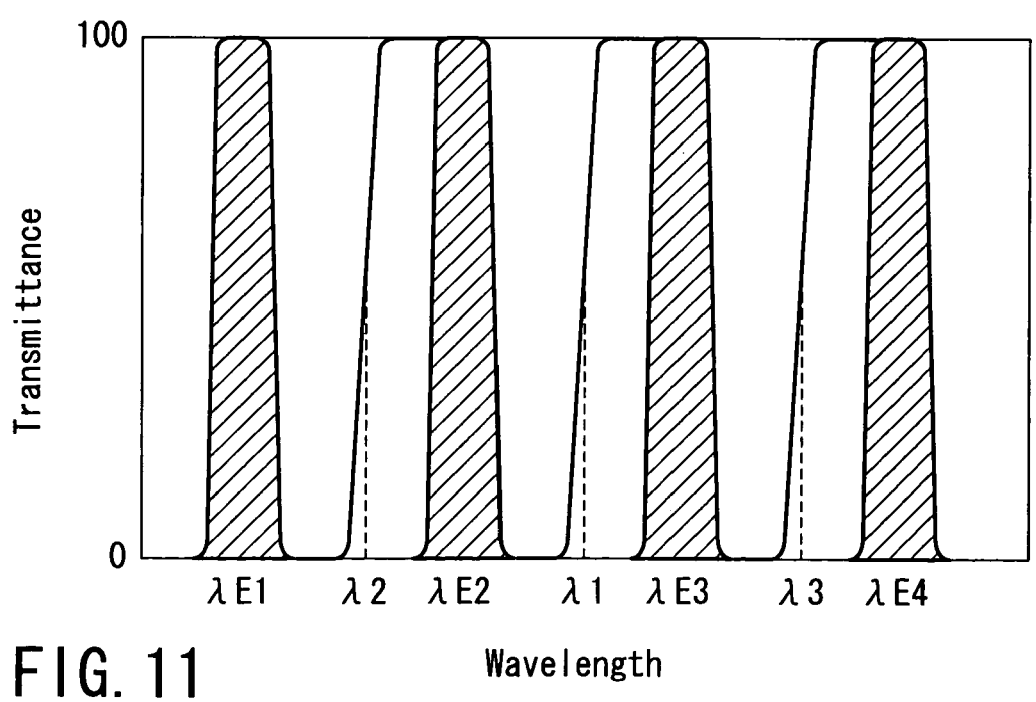
FIG. 11 is a diagram showing a relation between wavelengths separated by each dichroic mirror and emission filter in the TIRFM.

FIG. 11 is a diagram showing a relation among the wavelengths separated by the first to third dichroic mirrors 93, 94, 99 and the first to fourth emission filters 22, 95, 100, 102. The respective specific wavelength bands $\lambda_{E1}$ to $\lambda_{E4}$ have a relation of $\lambda_{E1} < \lambda_{E2} < \lambda_{E3} < \lambda_{E4}$.

Next, the operation of the TIRFM constituted as described above will be described.

The laser oscillation unit 32 in the first laser introduction section $L_1$ oscillates the laser beam having the wavelength $\lambda_{L1}$. The laser beam having the wavelength $\lambda_{L1}$ is introduced into the optical fiber 33, and is emitted as a divergent ray from the fiber emission end 34. The laser beam emitted as the divergent ray is converted to the convergent ray through the condensing lens 36, and is incident upon the reflective mirror 47.

The laser beam incident upon the reflective mirror 47 is reflected on the condenser lens 27 side in the vicinity of the outermost side of the transmitted illuminative light path T. The laser beam reflected by the reflective mirror 47 is once condensed in the vicinity of the front focal position of the condenser lens 27 by the condensing lens 36. Moreover, the laser beam is incident upon the condenser lens 27, and is emitted as the parallel ray advancing in the oblique direction from the condenser lens 27. The laser beam emitted from the condenser lens 27 is transmitted through the immersion oil 6 and is incident upon the boundary surface between the slide glass 24 and specimen 25.

When the incidence angle $\theta_{L1}$ of the laser beam upon the boundary surface between the slide glass 24 and specimen 25 is larger than the critical angle of the total internal reflection, the laser beam is totally reflected by the boundary surface. Accordingly, the evanescent light leaks on the specimen 25 side.

The specific fluorescent substance existing in the specimen 25 is excited by the evanescent light having the wavelength $\lambda_{L1}$. By the excitation, the fluorescent substance emits the fluorescence such that the maximum luminance wavelength of the fluorescence is in the transmission wavelength band $\lambda_{E1}$ of the emission filter 22. The fluorescence is incident upon the objective lens 20 through the cover glass 26. Furthermore, the fluorescence is transmitted through the image forming lens 21 and emission filter 22, and is incident upon the first image pick-up device 23. The first image pick-up device 23 picks up the fluorescent image of the wavelength band $\lambda_{E1}$.

On the other hand, when the micrometer operation section 45 in the first laser introduction section $L_1$ is rotated, the reflective mirror 47 moves in the translatory manner in the direction crossing the transmitted illuminative light path T substantially at right angles. When the position of the reflective mirror 47 moves in the direction crossing the transmitted illuminative light path T substantially at right angles, the incidence position of the laser beam upon the condenser lens 27 moves. Accordingly, the emission angle of the laser beam emitted from the condenser lens 27, that is, the incidence angle $\lambda_{L1}$ of the laser beam upon the boundary surface between the slide glass 24 and specimen 25 changes.

The leak-out depth of the evanescent light in the total internal reflection illumination changes with the incidence angle $\theta_{L1}$ of the laser beam upon the boundary surface between the slide glass 24 and specimen 25. Therefore, the micrometer operation section 45 is rotated to slightly move the reflective mirror 47 in the direction crossing the transmitted illuminative light path T substantially at right angles. That is, when the reflective mirror 47 is brought close to or far from the transmitted illuminative light path T, the leak-out depth $d_{L1}$ of the evanescent light can be optionally changed.

It is to be noted when the transmission illuminative observation is performed using the illuminative light output from the transmitted illuminative light source 31, the reflective mirror 47 is completely retreated from the transmitted illuminative light path T.

The second laser introduction section $L_2$ is similar to the first laser introduction section $L_1$. When the micrometer operation section 45 in the second laser introduction section $L_2$ is rotated, an incidence angle $\theta_{L2}$ of the laser beam having a wavelength $\lambda_{L2}$ incident upon the boundary surface between the slide glass 24 and specimen 25 changes. Accordingly, a leak-out depth $d_{L2}$ of the evanescent light can be optionally changed.

The specific fluorescent substance existing in the specimen 25 is excited by the evanescent light having the wavelength $\lambda_{L2}$. By the excitation, the specific fluorescent substance existing in the specimen 25 emits the fluorescence such that the maximum luminance wavelength of the fluorescence exists in a transmission wavelength band $\lambda_{E2}$ of the second emission filter 95. The fluorescence of the wavelength band $\lambda_{E2}$ is incident upon the objective lens 20 through the cover glass 26.

The fluorescence of the wavelength band $\lambda_{E2}$ through the objective lens 20 is reflected by the first dichroic mirror 93 in the observation optical path Q, and is incident upon the second dichroic mirror 94 through the image forming lens 21. The fluorescence of the wavelength band $\lambda_{E2}$ is reflected by the second dichroic mirror 94, transmitted through the second emission filter 95, and incident upon the second image pick-up device 96. The second image pick-up device 96 picks up the fluorescent image of the wavelength band $\lambda_{E2}$.

The third and fourth laser introduction sections $L_3$, $L_4$ are also similar to the first laser introduction section $L_1$. When the micrometer operation-section 45 in the third laser introduction section $L_3$ is rotated, an incidence angle $\theta_{L3}$ of the laser beam having a wavelength $\lambda_{L3}$ incident upon the boundary surface between the slide glass 24 and specimen 25 changes. Accordingly, a leak-out depth $d_{L3}$ of the evanescent light having the wavelength $\lambda_{L3}$ can be optionally changed.

The fluorescence having a wavelength band $\lambda_{E3}$ is transmitted through the first dichroic mirror 93, and is incident upon the third dichroic mirror 99 through the second image forming lens 97 and total internal reflection prism 98. The fluorescence of the wavelength band $\lambda_{E3}$ is reflected by the third dichroic mirror 99, transmitted through the third emission filter 100, and incident upon the third image pick-up device 101. The third image pick-up device 101 picks up the fluorescent image of the wavelength band $\lambda_{E3}$. When the micrometer operation section 45 in the fourth laser introduction section $L_4$ is rotated, an incidence angle $\theta_{L4}$ of the laser beam having a wavelength $\lambda_{L4}$ incident upon the boundary surface between the slide glass 24 and specimen 25 changes. Accordingly, a leak-out depth $d_{L4}$ of the evanescent light having the wavelength $\lambda_{L4}$ can be optionally changed.

The fluorescence of a wavelength band $\lambda_{E4}$ is transmitted through the first dichroic mirror 93, passed through the second image forming lens 97 and total internal reflection prism 98, and incident upon the third dichroic mirror 99. The fluorescence of the wavelength band $\lambda_{E4}$ is transmitted through the third dichroic mirror 99, transmitted through the fourth emission filter 102, and incident upon the fourth image pick-up device 103. The fourth image pick-up device 103 picks up a fluorescent image of the wavelength band $\lambda_{E4}$.

As described above, according to the fifth embodiment, each maximum incidence angle θmax of the laser beams having the wavelengths $\lambda_{L1}$ to $\lambda_{L4}$ incident upon the boundary surface between the slide glass 24 and specimen 25 depends only on the NA of the condenser lens 27 in the same manner as in the first embodiment. Therefore, the fluorescence observation by the total internal reflection illumination is possible regardless of the NA or the magnification of the objective lens 20.

The first to fourth laser introduction sections $L_1$, $L_2$, $L_3$, $L_4$ a are disposed apart from the specimen 25 and condenser lens 27. Accordingly, there is not any structure disposed in the vicinity of the specimen 25, and the space in the vicinity of the specimen 25 is not compressed. The first to fourth laser introduction sections $L_1$, $L_2$, $L_3$, $L_4$ can be radially disposed on the base 28.

The first to fourth laser introduction sections $L_1$, $L_2$, $L_3$, $L_4$ include the structure in which the reflective mirror 47 is moved by the micrometer 43. The first to fourth laser introduction sections $L_1$, $L_2$, $L_3$, $L_4$ have the simple structure and also have the narrow operation range. Therefore, for the first to fourth laser introduction sections $L_1$, $L_2$, $L_3$, $L_4$, the TIRFM itself can be compact, and the TIRFM can have the superior operation property.

For the first to fourth laser introduction sections $L_1$, $L_2$, $L_3$, $L_4$, the respective wavelengths $\lambda_{L1}$ to $\lambda_{L4}$ and the leak-out depths $d_{L1}$ to $d_{L4}$ of the evanescent light can be individually set.

Therefore, each portion in the specimen 25 which is an observation object is sometimes labeled using a plurality of types of fluorescent substances such as CFP, GFP, YFP, RFP. In this case, it is possible to adjust the leak-out depth of the evanescent light having a wavelength for excitation to be optimum in accordance with the depth in which each portion to be labeled is positioned.

The first to fourth laser introduction sections $L_1$, $L_2$, $L_3$, $L_4$ are constituted completely independently of one another. Accordingly, optical characteristics can be independently set in accordance with user's application. In addition to the first to fourth laser introduction sections $L_1$, $L_2$, $L_3$, $L_4$, it is possible to dispose, add, or remove the necessary number of laser introduction sections. That is, the laser introduction sections can further be added to an extra space if any.

An illuminating side (condenser lens 27 side) is separated from an observation side (objective lens 20 side). Accordingly, the dichroic mirror of the multi-band is not required, and the handling is facilitated.

Therefore, according to the fifth embodiment, a total internal reflection fluorescence microscope having the following superior system property can be provided. The microscope is compact and is easily handled. A plurality of laser introduction sections can easily be added. The leak-out depths of the evanescent light can be independently set using laser beams having a plurality of wavelengths. It is possible to simultaneously irradiate the specimen 25 with the laser beam having a plurality of wavelengths.

It is to be noted that the fifth embodiment may also be modified as follows.

The glass bottom dish may also be used instead of the slide glass 24. Accordingly, the cover glass 26 may be omitted. In this case, when the operating distance of the objective lens 20 is short, the immersion objective lens is used.

The reflective mirror 47 may also be moved using, for example, the electromotive motor, piezo-actuator or the like in addition to the micrometer.

The reflective mirror 47 is fixed. The fiber emission end 34 and condensing lens 36 may be integrally moved in the direction parallel to the optical axis of the transmitted illuminative light path T. The fiber emission end 34 and condensing lens 36 are movable, for example, using the micro-motor, electromotive motor, piezo-actuator, or the like.

The embodiment is applicable not only to the erected type microscope but also to the inverted microscope.

The constitution on the observation optical path Q may also be optional as long as the fluorescence wavelength with respect to each excitation wavelength is selected to pick up the image.

Figure 12:
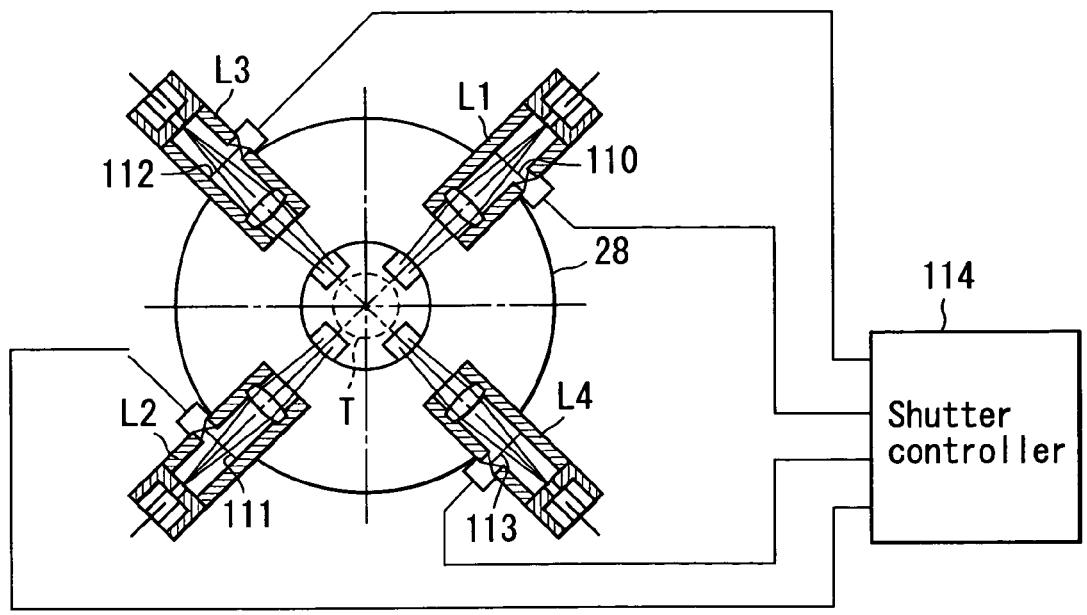
FIG. 12 is a constitution diagram showing a modification of the TIRFM.

As shown in FIG. 12, shutters 110 to 113 may also be disposed in the respective first to fourth laser introduction sections $L_1$, $L_2$, $L_3$, $L_4$. The respective shutters 110 to 113 select the introducing and blocking of the laser beam in the respective first to fourth laser introduction sections $L_1$, $L_2$, $L_3$, $L_4$. A shutter controller 114 individually controls the opening/closing of each of the shutters 110 to 113. Accordingly, the laser beam to be introduced into the specimen 25 can be selected.

The wavelength of each laser beam introduced from a plurality of laser introduction sections, for example, at least two laser introduction section among the first to fourth laser introduction sections $L_1$, $L_2$, $L_3$, $L_4$ is set to be equal. Moreover, the respective laser beams are alternately introduced into the specimen 25 by the opening/closing of the respective shutters, for example, the shutters 110, 111. Accordingly, the leak-out depth of each evanescent light generated by the excitation of each laser beam is changed. As a result, when the observed images by the difference in the leak-out depth of the fluorescence by the same fluorescent substance are compared, it is possible to specify the depth of a generation source of the fluorescence.

The laser oscillation units such as laser diodes for use in the first to fourth laser introduction sections $L_1$, $L_2$, $L_3$, $L_4$ oscillate the laser beams having the single wavelength. The present invention is not limited to this, and the laser oscillation unit may also oscillate a laser beam having a multi-wavelength.

Figure 13:
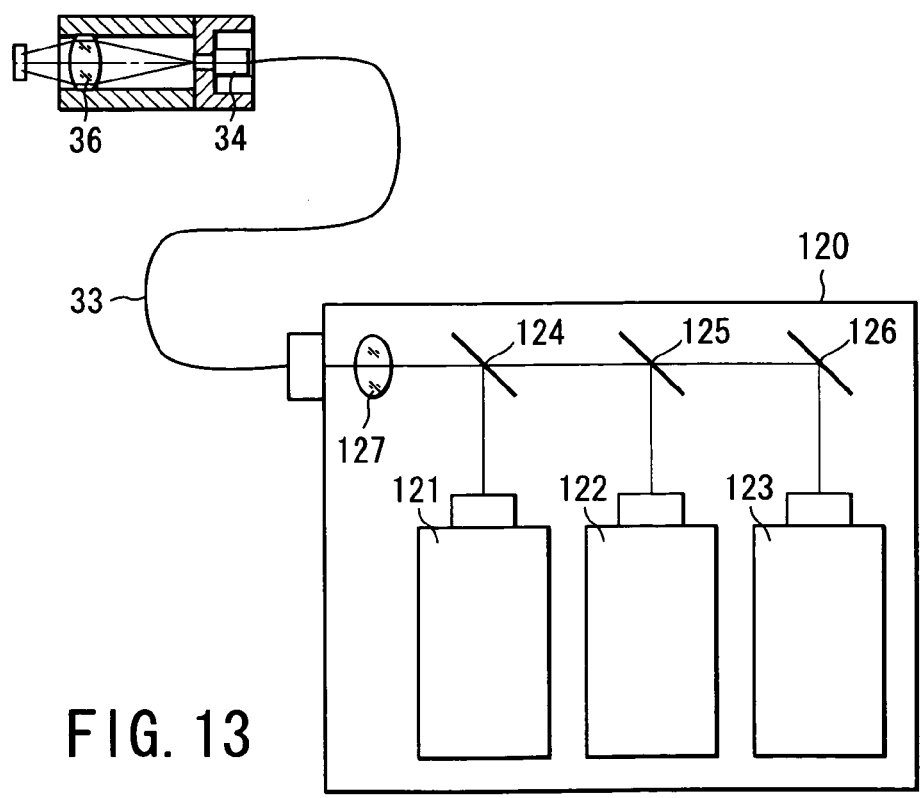
FIG. 13 is a constitution diagram of a laser combiner in the TIRFM.

For example, a laser combiner 120 shown in FIG. 13 may also be used. The laser combiner 120 includes laser oscillation units 121 to 123 which oscillate the respective laser beams having different wavelengths. Dichroic mirrors 124, 125 are disposed on the optical paths of the laser beams output from the laser oscillation units 121, 122. A mirror 126 is disposed on the optical path of the laser beam output from the laser oscillation unit 123. The dichroic-mirrors 124, 125 and condensing lens 127 are disposed on the reflective optical paths of the mirror 126.

With this constitution, the laser beam emitted from the laser oscillation unit 123 is reflected by the mirror 126. The respective laser beams emitted from the laser oscillation units 121, 122 are reflected by the dichroic mirrors 124, 125. Accordingly, the laser beams emitted from the laser oscillation units 121, 122 are synthesized with the laser beam emitted from the laser oscillation unit 123. The synthesized laser beams are condensed on the optical fiber 33 by the objective lens 74. As a result, the synthesized laser beam having each wavelength is transmitted through the optical fiber 33, and sent to the conversion lens unit 50.

A plurality of fluorescent substances having different excitation wavelength regions in one laser introduction section can be excited using the laser beam having the multi-wavelength.

For the respective laser introduction sections $L_1$, $L_2$, $L_3$, $L_4$, as shown in FIGS. 3 and 4, the conversion lens unit 50 may also be detachably attached between the fiber emission end 34 of the optical fiber 33 and the condensing lens 36.

The present invention is also applicable to a microscope including a plurality of objective lenses having different observation magnifications, for example, the objective lens for high-magnification observation 61 and objective lens for low-magnification observation 62 shown in FIG. 5. With the application to the microscope, when the objective lens for high-magnification observation 61 is disposed on the observation optical path Q, the conversion lens unit 50 is inserted into the laser introductory optical path in each of the laser introduction sections $L_1$, $L_2$, $L_3$, $L_4$. When the objective lens for low-magnification observation 62 is inserted into the observation optical path Q, the conversion lens unit 50 is detached from the laser introductory optical path in each of the laser introduction sections $L_1$, $L_2$, $L_3$, $L_4$.

For the respective laser introduction sections $L_1$, $L_2$, $L_3$, $L_4$, the zoom lens unit 69 shown in FIGS. 7A and 7B is applicable.

Figure 10:
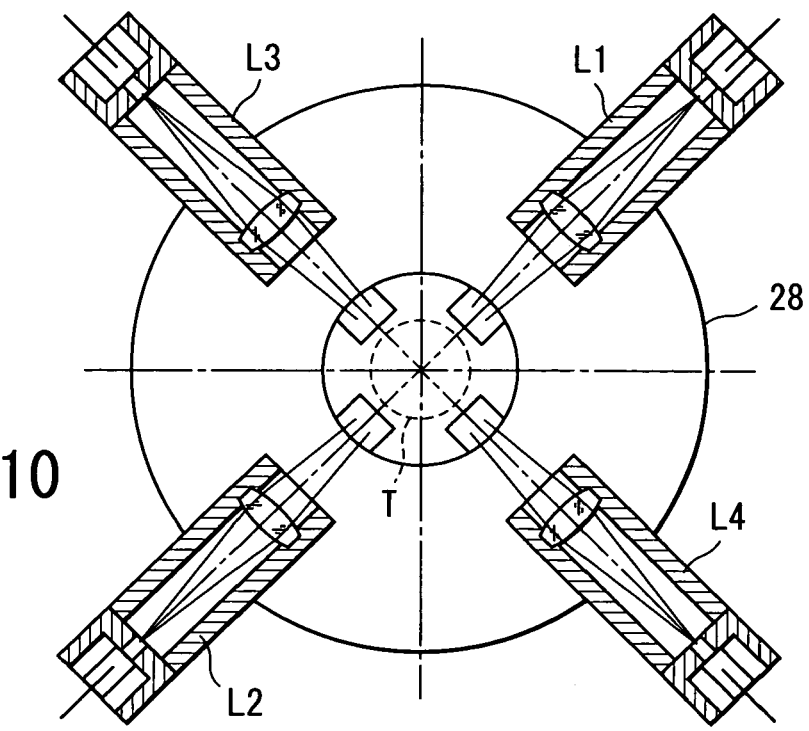
FIG. 10 is a diagram showing an arrangement of each laser introduction section in the TIRFM.

A sixth embodiment of the present invention will be described with reference to the drawings. It is to be noted that the same parts as those of FIGS. 9 and 10 are denoted with the same reference numerals and detailed description thereof is omitted.

Figure 14:
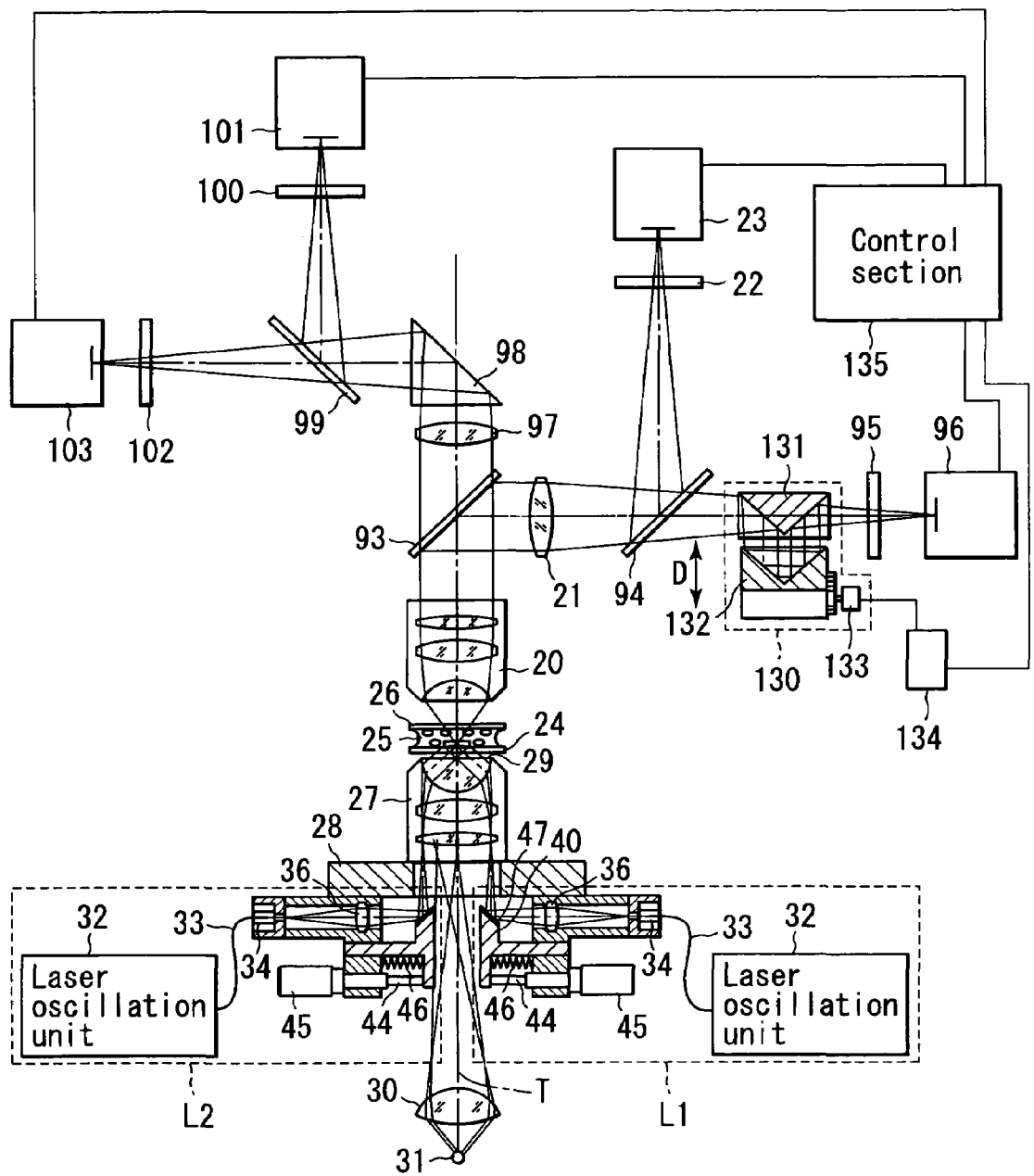
FIG. 14 is a constitution diagram showing a fifth embodiment of the TIRFM of the present invention.

FIG. 14 is a constitution diagram of the erected type total internal reflection fluorescence microscopy (TIRFM). An optical path length adjustment section 130 is disposed on the optical path between the second dichroic mirror 94 and the second emission filter 95. The optical path length adjustment section 130 includes a fixed prism group 131, movable prism 132, and prism moving section 133.

The movable prism 132 is movable in a direction (arrow D direction) vertical to the optical path between the second dichroic mirror 94 and the second emission filter 95. That is, the movable prism 132 is movable in a leaving direction and an approaching direction with respect to the fixed prism group 131.

The prism moving section 133 linearly drives the movable prism 132 in the leaving direction and the approaching direction with respect to the fixed prism group 131. The prism moving section 133 uses, for example, the electromotive motor, piezo-actuator or the like in order to move the movable prism 132 in the translatory manner.

Therefore, the optical path length adjustment section 130 linearly drives the movable prism 132 in the leaving direction and the approaching direction with respect to the fixed prism group 131 to extend the image forming position of the fluorescence emitted from the fluorescent substance of the specimen 25. A reference position in extending the image forming position of the fluorescence is the image forming position of the first image forming lens 21.

The prism moving section 133 is connected to a control section 135 via a driver 134. The driver 134 receives a driving signal emitted from the control section 135 to drive the prism moving section 133.

The control section 135 includes the personal computer and the like. The control section 135 transmits the driving command to the driver 134 to drive the movable prism 132 in the leaving direction or the approaching direction with respect to the fixed prism group 131 in the translatory manner. The control section 135 processes image signals output from the first to fourth image pick-up devices 23, 96, 101, 103 into images, respectively.

Figure 15:
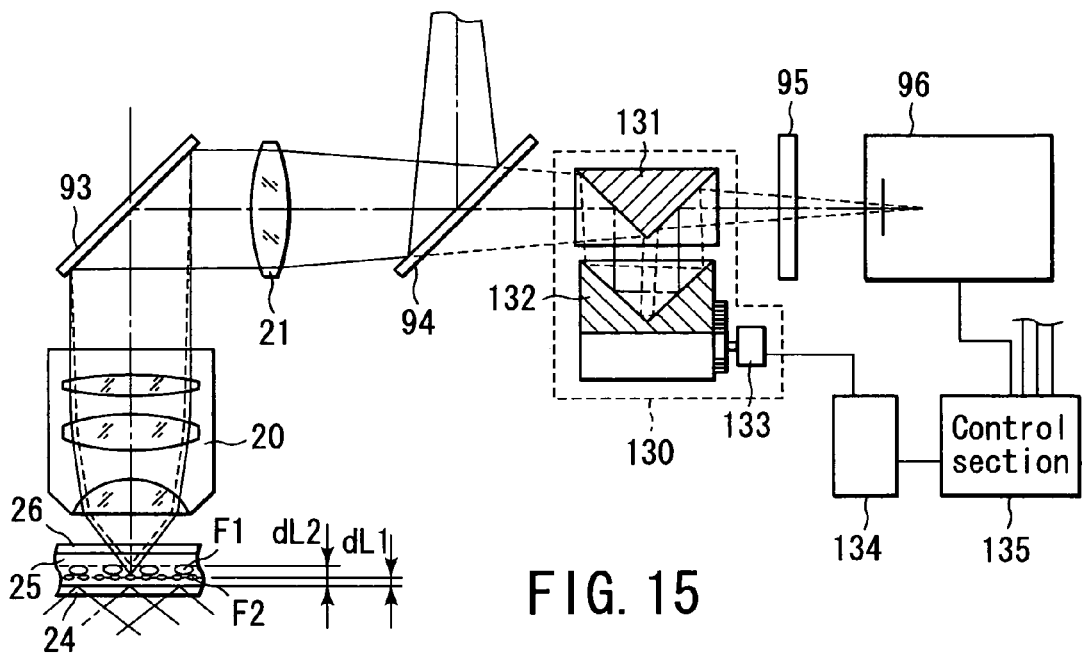
FIG. 15 is an enlarged view of the inside of the specimen and an observation optical path in the TIRFM.

FIG. 15 is an enlarged view of the inside of the specimen and the observation optical path. A first fluorescent substance $F_1$ is excited by the wavelength $\lambda_{L1}$ of the laser beam introduced from the laser introduction section $L_1$ to emit the fluorescence. The maximum luminance wavelength of the fluorescence is in the transmission wavelength band $\lambda_{E1}$ of the first emission filter 22.

A second fluorescent substance $F_2$ is excited by the wavelength $\lambda_{L2}$ of the laser beam introduced from the laser introduction section $L_2$ to emit the fluorescence. The maximum luminance wavelength of the fluorescence is in the transmission wavelength band $\lambda_{E2}$ of the second emission filter 95.

The first and second fluorescent substances $F_1$, $F_2$ are introduced into the cell in the specimen 25 so as to be peculiarly developed in specific small organs. The first fluorescent substance $F_1$ is developed in the small organ in the vicinity of the cell film. The second fluorescent substance $F_2$ is developed in the small organ positioned slightly distant from the cell film.

The leak-out depth $d_{L1}$ of the evanescent light for exciting the fluorescent substance $F_1$ is set to be shallow. On the other hand, the leak-out depth $d_{L2}$ of the evanescent light for exciting the fluorescent substance $F_2$ is set to be larger than the leak-out depth $d_{L1}$.

A focal point of the objective lens 20 is adjusted to the small organ in which the first fluorescent substance $F_1$ is developed.

Therefore, the position of the small organ in which the second fluorescent substance $F_2$ is developed is in the vicinity of the objective lens 20 side rather than the focal position of the objective lens 20.

Next, the operation of the TIRFM constituted as described above will be described.

When the micrometer operation section 45 of the laser introduction section $L_1$ is rotated, the depth reaching the first fluorescent substance $F_1$ of the evanescent light having the wavelength $\lambda_{L1}$ is adjusted. Similarly, when the micrometer operation section 45 of the laser introduction section $L_2$ is rotated, the depth reaching the second fluorescent substance $F_2$ of the evanescent light having the wavelength $\lambda_{L2}$ is adjusted.

The first fluorescent substance $F_1$ is in the focal position of the objective lens 20. The fluorescence emitted from the first fluorescent substance $F_1$ turns to the parallel ray through the objective lens 20, is reflected by the first dichroic mirror 93, forms the convergent ray through the first image forming lens 21, is passed through the second dichroic mirror 94 and first emission filter 22, and is formed into the image on the image pick-up surface of the first image pick-up device 23.

On the other hand, the second fluorescent substance $F_2$ is in a position deviating on the objective lens 20 side from the focal position of the objective lens 20. The fluorescence emitted from the second fluorescent substance $F_2$ is passed through the objective lens 20 to form a slightly divergent ray as shown by a dotted line in FIG. 15. The fluorescence is reflected by the first dichroic mirror 93 and passed through the image forming lens 21 to form the convergent ray.

At this time, the image forming position after the second dichroic mirror 94, optical path length adjustment section C1, and second emission filter 95 corresponds to the position after the image pick-up surface of the second image pick-up device 96 in a state in which the movable prism 132 is in a standard position. Accordingly, the fluorescence image of the second fluorescent substance $F_2$ picked up by the second image pick-up device 96 forms an image which is out of focus.

The control section 135 emits the driving command to the driver 134. Accordingly, the prism moving section 133 moves the movable prism 132 in a direction distant from the fixed prism group 131 in the translatory manner. By the translatory movement, the optical path length is extended reaching the second image pick-up device 96. The image forming position of the fluorescence emitted from the second fluorescent substance $F_2$ is close to the image pick-up surface of the second image pick-up device 96.

Figure 16:
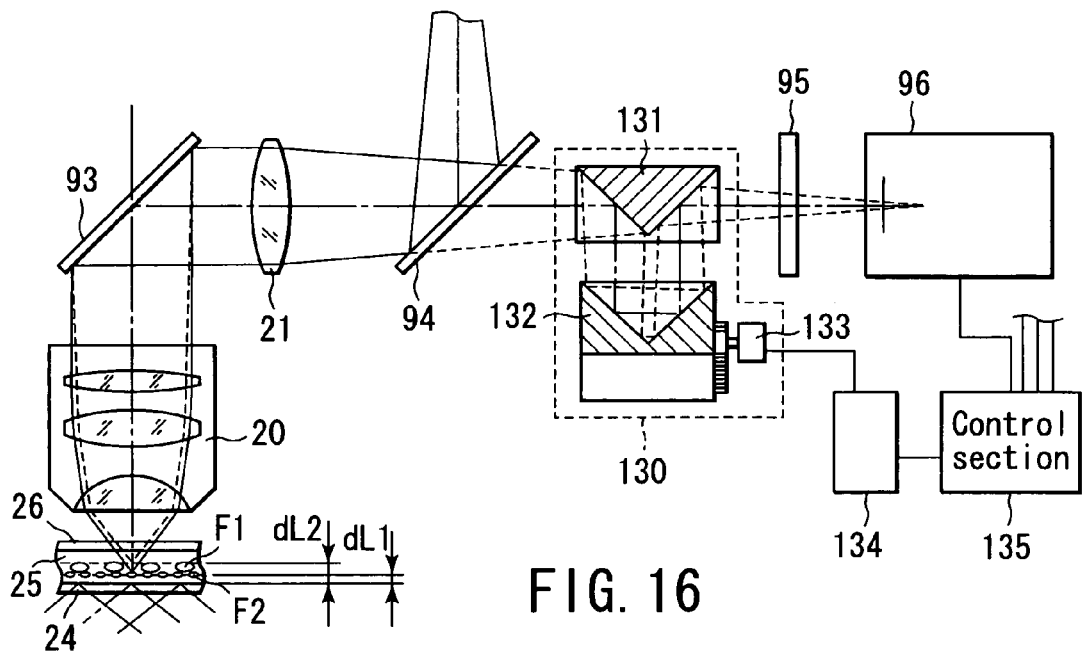
FIG. 16 is a diagram showing a state in which an image forming position of fluorescence emitted from a fluorescent substance agrees with an image pick-up surface of an image pick-up device in the TIRFM.
Figure 17A:
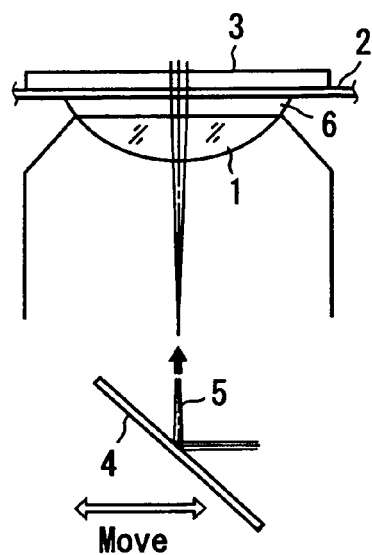
FIG. 17A is a diagram showing a function of a conventional TIRFM.
Figure 17B:
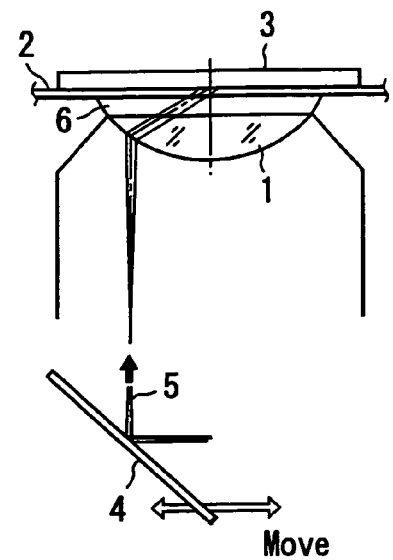
FIG. 17B is a diagram showing the function of the conventional TIRFM.
Figure 17C:
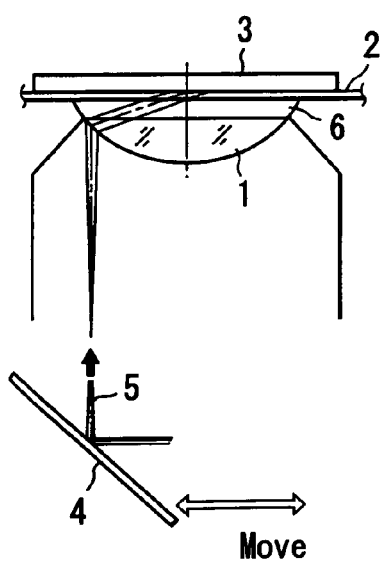
FIG. 17C is a diagram showing the function of the conventional TIRFM.
Figure 19:
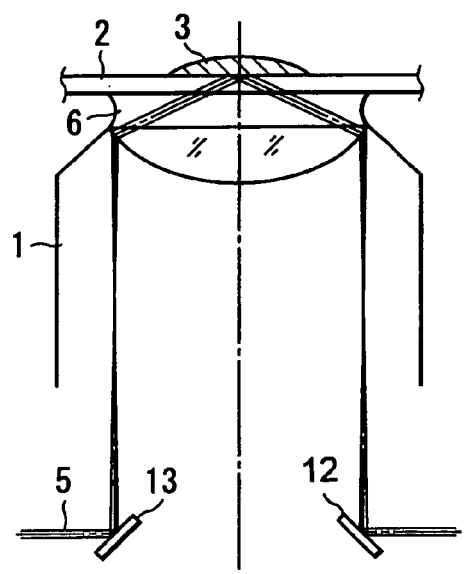
FIG. 19 is a constitution diagram of the conventional TIRFM.
Figure 18:
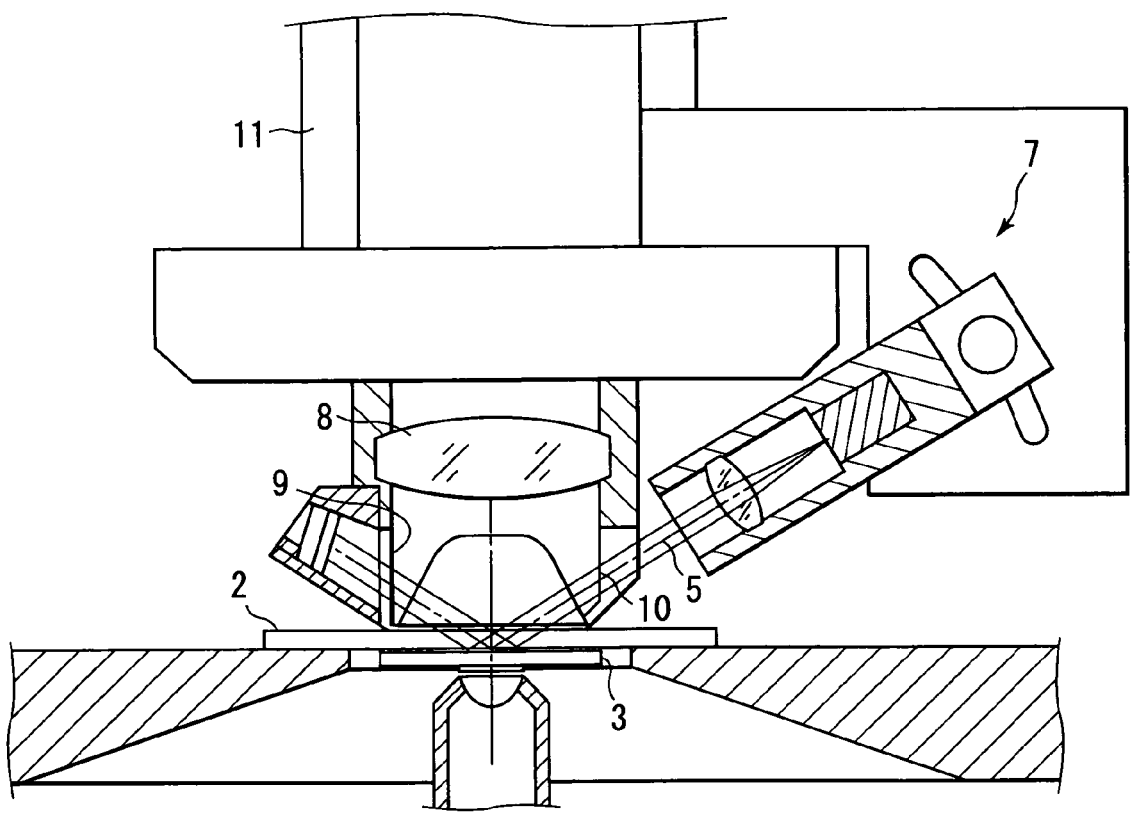
FIG. 18 is a constitution diagram of the conventional TIRFM.

FIG. 16 shows a state in which the image forming position of the fluorescence emitted from the second fluorescent substance $F_2$ agrees with the image pick-up surface of the second image pick-up device 96. The fluorescence emitted from the second fluorescent substance $F_2$ in the position deviating on the objective lens 20 side from the focal position of the objective lens 20 is formed into the image on the image pick-up surface of the second image pick-up device 96.

At this time, the control section 135 calculates positional deviation of the second fluorescent substance $F_2$ with respect to the focal position of the objective lens 20 based on the movement from the reference position of the movable prism 132. Moreover, the control section 135 calculates a deviation of enlargement magnification on the image pick-up surface of the second image pick-up device 96. Moreover, the control section 135 performs an image processing to correct the magnification of the picked-up image.

As described above, according to the sixth embodiment, the objective lens 20 is fixed, and the surfaces having the different depths on the specimen 25 are subjected to total internal reflection illumination, and can be simultaneously observed with high contrast. For example, small organs in the different depth positions on the specimen 25 such as the small organ in which the first fluorescent substance $F_1$ is developed and the small organ in which the second fluorescent substance $F_2$ is developed are subjected to the total internal reflection illumination, and can be simultaneously observed with the high contrast.

The sixth embodiment may also be modified as follows.

An optical path length adjustment section constituted in the same manner as in the optical path length adjustment section 130 may also be disposed on each of divided observation optical paths extending to image pick-up devices other than the second image pick-up device 96, such as the first, third and fourth image pick-up devices 23, 101, 103. In this case, the driver 134 includes a plurality of channels for driving a plurality of optical path length adjustment sections. The respective channels are independently controlled by the driving command from the control section 135.

A similar effect is obtained, for example, even when the second image pick-up device 96 itself is linearly moved in a direction parallel to the optical path instead of disposing the optical path length adjustment section 130. The similar effect is obtained, for example, even when the first, third and fourth image pick-up devices 23, 101, 103 are translatorily moved in the direction parallel to the optical path.

The shutters 110 to 113 may also be disposed in each of the first to fourth laser introduction sections $L_1$, $L_2$, $L_3$, $L_4$ in the same manner as in FIG. 12. When the opening/closing of the respective shutters 110 to 113 is controlled by the shutter controller, the laser beam to be introduced into the specimen 25 can be selected.

The wavelengths of the laser beams introduced from a plurality of laser introduction sections, for example, at least two laser introduction sections among the first to fourth laser introduction sections $L_1$, $L_2$, $L_3$, $L_4$ are set to be equal. Moreover, the respective laser beams are alternately introduced into the specimen 25, for example, by the opening/closing the shutters 110, 111. Accordingly, the leak-out depth of the evanescent light generated by the excitation of each laser beam is changed. As a result, when the observed images by the difference in the leak-out depth of the fluorescence by the same fluorescent substance are compared, it is possible to specify the depth of the generation source of the fluorescence.

What is claimed is:

1. A total internal reflection fluorescence microscope comprising:
   at least one objective lens which takes light from a specimen;
   an image pick-up device which picks up an image of the light taken into the objective lens;
   an observation optical path via which the light taken into the objective lens is condensed onto the image pick-up device;
   a condenser lens, which is disposed in a position facing the objective lens via the specimen, which has a numerical aperture that makes possible total internal reflection illumination, and which guides a transmitted illuminative light, which is emitted by a light source, into the specimen;
   a base including an upper portion that holds the condenser lens;
   a laser oscillation unit which outputs a laser beam;
   an optical fiber which transmits the laser beam output from the laser oscillation unit;
   a reflection mirror provided at a lower portion of the base to reflect the laser beam output from the optical fiber along a path substantially parallel to a light path of the transmitted illuminative light from the light source, so as to introduce the laser beam into a vicinity of an outermost side of the condenser lens;
   a condensing lens which condenses the laser beam output from the optical fiber, such that the laser beam is condensed at a condensing position in a vicinity of a front focal position of the condenser lens; and
   a mirror moving section which moves the reflection mirror in a translatory manner, with respect to the condensing lens, in a direction that is substantially perpendicular to the light path of the transmitted illuminative light from the light source, such that when the mirror moving section moves the reflection mirror, the path of the laser beam reflected by the reflection mirror remains substantially parallel to the light path of the transmitted illuminative light,
   wherein when the mirror moving section moves the reflection mirror with respect to the condensing lens, an incidence angle, at a boundary of the specimen, of the laser beam emitted from the condenser lens is changed, thereby changing a leak-out depth of evanescent light that illuminates the specimen.

2. The total internal reflection fluorescence microscope according to clam 1, further comprising a conversion lens unit which converts a numerical aperture of the laser beam incident upon the condensing position without changing the condensing position of the laser beam.

3. The total internal reflection fluorescence microscope according to claim 2, wherein the conversion lens unit is removably inserted between an emission end of the optical fiber and the condensing lens.

4. The total internal reflection fluorescence microscope according to claim 2, wherein the conversion lens unit includes a lens group which converts a numerical aperture of the laser beam incident upon the condensing position.

5. The total internal reflection fluorescence microscope according to claim 2, wherein the conversion lens unit comprises:
   a convex lens which converts the numerical aperture of the laser beam diverged and emitted from an emission end of the optical fiber; and
   a concave lens which diverges the laser beam having the numerical aperture converted by the convex lens.

6. The total internal reflection fluorescence microscope according to claim 5, wherein the concave lens is movable in an optical path direction of the laser beam between the convex lens and the condensing lens.

7. The total internal reflection fluorescence microscope according to claim 3, wherein the at least one objective lens comprises a plurality of objective lenses having different observation magnifications, and the microscope further comprises:
   an objective lens switching section which selectively disposes one of the plurality of objective lenses on the observation optical path; and
   a control section which controls inserting and removing of the conversion lens unit between the emission end of the optical fiber and the condensing lens in accordance with the observation magnification of the objective lens disposed on the observation optical path.

8. The total internal reflection fluorescence microscope according to claim 7, wherein the plurality of objective lenses include at least one objective lens for high-magnification observation and at least one objective lens for low-magnification observation, and
   wherein the control section inserts the conversion lens unit between the emission end of the optical fiber and the condensing lens when the objective lens for high-magnification observation is disposed on the observation optical path, and the control section removes the conversion lens unit from between the emission end of the optical fiber and the condensing lens when the objective lens for low-magnification observation is disposed on the observation optical path.

9. The total internal reflection fluorescence microscope according to claim 8, wherein an irradiation range of the laser beam with respect to the specimen is caused to agree with an observation range of the objective lens for high-magnification observation when the conversion lens unit is inserted between the emission end of the optical fiber and the condensing lens, and the irradiation range of the laser beam with respect to the specimen is caused to agree with an observation range of the objective lens for low-magnification observation when the conversion lens unit is removed from between the emission end of the optical fiber and the condensing lens.

10. The total internal reflection fluorescence microscope according to claim 1, further comprising a zoom lens unit which adjusts the condensing position of the laser beam in the vicinity of the front focal position of the condenser lens.

11. The total internal reflection fluorescence microscope according to claim 10, wherein the zoom lens unit comprises a lens group which adjusts the condensing position of the laser beam in the vicinity of the front focal position of the condenser lens.

12. The total internal reflection fluorescence microscope according to claim 10, wherein the zoom lens unit comprises:
a convex lens which converts the numerical aperture of the laser beam diverged and emitted from an emission end of the optical fiber; and
a concave lens which diverges the laser beam having the numerical aperture converted by the convex lens.

13. The total internal reflection fluorescence microscope according to claim 12, wherein the convex lens is movable in an optical path direction of the laser beam between the emission end of the optical fiber and the condensing lens.

14. The total internal reflection fluorescence microscope according to claim 12, wherein the concave lens is movable in an optical path direction of the laser beam between the convex lens and the condensing lens.

15. The total internal reflection fluorescence microscope according to claim 12, further comprising:
a control section which determines a moving position of the concave lens to adjust the condensing position of the laser beam in the vicinity of the front focal position of the condenser lens in accordance with positional movement of the convex lens, and which controls movement of the convex lens and the concave lens based on information of the determined moving position of the concave lens.

16. The total internal reflection fluorescence microscope according to claim 11, wherein the at least one objective lens comprises a plurality of objective lenses having different observation magnifications, and the microscope further comprises:
an objective lens switching section which selectively disposes one of the plurality of objective lenses on the observation optical path; and
a control section which determines a relative positional relation of the lens group disposed in the zoom lens unit in each optical axis direction in accordance with an observation magnification of the objective lens disposed on the observation optical path.

17. The total internal reflection fluorescence microscope according to claim 16, wherein the lens group of the zoom lens unit comprises:
a convex lens which converts the numerical aperture of the laser beam diverged and emitted from an emission end of the optical fiber; and
a concave lens which diverges the laser beam having the numerical aperture converted by the convex lens, and
wherein the control section determines a moving position of the concave lens to adjust the condensing position of the laser beam in the vicinity of the front focal position of the condenser lens in accordance with positional movement of the convex lens, and the control section controls movement of the convex lens and the concave lens based on information of the determined moving position of the concave lens.

18. The total internal reflection fluorescence microscope according to claim 1, wherein the laser oscillation unit, the optical fiber, the reflection mirror, the mirror moving section, and the condensing lens form at least a part of a laser introduction section, and the microscope comprises a plurality of said laser introduction sections, each of which emits a laser beam that is condensed at a corresponding condensing position in a vicinity of corresponding front focal positions of the condenser lens; and
wherein the microscope further comprises:
at least one additional image pick-up device which picks up an image of the light taken into the objective lens;
at least one additional observation optical path via which the light taken into the objective lens is condensed onto the additional image pick-up device;
an optical dividing system which divides the light taken into the objective lens onto respective ones of the optical paths toward the image pick-up devices depending on optical characteristics of the light.

19. The total internal reflection fluorescence microscope according to claim 18, wherein each of the plurality of laser introduction sections comprises a conversion lens unit which converts a numerical aperture of the laser beam incident upon the condensing position without changing the condensing position of the laser beam.

20. The total internal reflection fluorescence microscope according to claim 19, each said conversion lens unit is removably inserted between an emission end of the optical fiber and the condensing lens in the corresponding one of the laser introduction sections.

21. The total internal reflection fluorescence microscope according to claim 19, wherein each said conversion lens unit includes a lens group which converts a numerical aperture of the laser beam incident upon the corresponding condensing position.

22. The total internal reflection fluorescence microscope according to claim 19, each said conversion lens unit comprises:
a convex lens which converts the numerical aperture of the laser beam diverged and emitted from an emission end of the optical fiber in the corresponding one of the laser introduction sections; and
a concave lens which diverges the laser beam having the numerical aperture converted by the convex lens.

23. The total internal reflection fluorescence microscope according to claim 22, wherein each said concave lens is movable in an optical path direction of the laser beam between the convex lens and the condensing lens in the corresponding one of the laser introduction sections.

24. The total internal reflection fluorescence microscope according to claim 20, wherein the at least one objective lens comprises a plurality of objective lenses having different observation magnifications, and the microscope further comprises:
an objective lens switching section which selectively disposes one of the plurality of objective lenses to take the light from the specimen; and
a control section which controls inserting and removing of the conversion lens unit in each of the plurality of laser introduction sections between the emission end of the optical fiber and the condensing lens in accordance with the observation magnification of the objective lens disposed to take the light from the sample.

25. The total internal reflection fluorescence microscope according to claim 24, wherein a plurality of objective lenses include at least one objective lens for high-magnification observation and at least one objective lens for low-magnification observation, and
wherein the control section inserts the conversion lens unit in each of the plurality of laser introduction sections between the emission end of the optical fiber and the condensing lens when the objective lens for high-magnification observation is disposed to take the light from the sample, and removes the conversion lens unit in each of the plurality of laser introduction sections between the emission end of the optical fiber and the condensing lens when the objective lens for low-magnification observation is disposed to take the light from the sample.

26. The total internal reflection fluorescence microscope according to claim 25, wherein, for each of the laser introduction sections, an irradiation range of the laser beam with respect to the specimen is caused to agree with an observation range of the objective lens for high-magnification observation when the conversion lens unit is inserted between the emission end of the optical fiber and the condensing lens, and the irradiation range of the laser beam with respect to the specimen is caused to agree with an observation range of the objective lens for low-magnification observation when the conversion lens unit is inserted between the emission end of the optical fiber and the condensing lens.

27. The total internal reflection fluorescence microscope according to claim 18, wherein each of the plurality of laser introduction sections further comprises a zoom lens unit which adjusts the condensing position of the laser beam in the vicinity of the front focal position of the condenser lens.

28. The total internal reflection fluorescence microscope according to claim 27, wherein each said zoom lens unit comprises a lens group which adjusts the condensing position of the laser beam in the vicinity of the front focal position of the condenser lens.

29. The total internal reflection fluorescence microscope according to claim 27, wherein the lens group of each said zoom lens unit comprises:
    a convex lens which converts the numerical aperture of the laser beam diverged and emitted from an emission end of the optical fiber in the corresponding laser introduction section; and
    a concave lens which diverges the laser beam having the numerical aperture converted by the convex lens.

30. The total internal reflection fluorescence microscope according to claim 29, wherein each said convex lens is movable in an optical path direction of the laser beam between the emission end of the optical fiber and the condensing lens in the corresponding one of the laser introduction sections.

31. The total internal reflection fluorescence microscope according to claim 29, wherein each said concave lens is movable in an optical path direction of the laser beam between the convex lens and the condensing lens in the corresponding one of the laser introduction sections.

32. The total internal reflection fluorescence microscope according to claim 29, further comprising:
    a control section which determines, for each said zoom lens unit, a moving position of the concave lens to adjust the condensing position of the laser beam in the vicinity of the front focal position of the condenser lens in accordance with positional movement of the convex lens, and which controls movement of the convex lens and the concave lens based on information of the determined moving position of the concave lens.

33. The total internal reflection fluorescence microscope according to claim 28, wherein the at least one objective lens comprises a plurality of objective lenses having different observation magnifications, and the microscope further comprises:
    an objective lens switching section which selectively disposes one of the plurality of objective lenses to take the light from the specimen; and
    a control section which determines a relative positional relation of the lens groups disposed in the zoom lens units in each optical axis direction in accordance with an observation magnification of the objective lens disposed on the observation optical path.

34. The total internal reflection fluorescence microscope according to claim 33, wherein the lens group of each said zoom lens unit comprises:
    a convex lens which converts the numerical aperture of the laser beam diverged and emitted from an emission end of the optical fiber in the corresponding laser introduction section; and
    a concave lens which diverges the laser beam having the numerical aperture converted by the convex lens, and
    wherein, for each of the zoom lens units, the control section determines a moving position of the concave lens to adjust the condensing position of the laser beam in the vicinity of the front focal position of the condenser lenses in accordance with positional movement of the convex lens, and the control section controls movement of the convex lens and the concave lens based on information of the determined moving position of the concave lens.

35. The total internal reflection fluorescence microscope according to claim 18, wherein the plurality of laser introduction sections are disposed radially around the transmitted illuminative light path and extend in directions that are substantially perpendicular to a path of the transmitted illuminative light.

36. The total internal reflection fluorescence microscope according to claim 18, further comprising:
    at least one optical path length adjustment section which is disposed on at least one divided observation optical path among the plurality of divided observation optical paths divided by the optical dividing system and which extends and contracts an optical path length.

37. The total internal reflection fluorescence microscope according to claim 36, wherein the optical path length adjustment section comprises:
    a fixed prism group fixed/disposed on the divided observation optical path; and
    a movable prism which is movable away from and toward the fixed prism group.

38. The total internal reflection fluorescence microscope according to claim 36, further comprising:
    a control section which calculates/processes an extension/contraction of the optical path length by the optical path length adjustment section.

39. The total internal reflection fluorescence microscope according to claim 18, further comprising:
    a plurality of shutters disposed in the plurality of laser introduction sections; and
    a control section which controls opening and closing of the plurality of shutters to control introducing and blocking of the laser beams from the laser introduction sections.

40. The total internal reflection fluorescence microscope according to claim 18, wherein the plurality of laser introduction sections includes at least two laser introduction sections which output laser beams a same wavelength.

41. A total internal reflection fluorescence microscope comprising:
    at least one objective lens which takes light from a specimen;
    an image pick-up device which picks up an image of the light taken into the objective lens;
    an observation optical path via which the light taken into the objective lens is condensed onto the image pick-up device;

a condenser lens, which is disposed in a position facing the objective lens via the specimen, which has a numerical aperture that makes possible total internal reflection illumination, and which guides a transmitted illuminative light, which is emitted by a light source, into the specimen;

a base including an upper portion that holds the condenser lens;

a laser oscillation unit which outputs a laser beam;

a laser introduction section which comprises a reflection mirror provided at a lower portion of the base to reflect the laser beam output from the laser oscillation unit along a path substantially parallel to a light path of the transmitted illuminative light from the light source, so as to introduce the laser beam into a vicinity of an outermost side of the condenser lens; and a mirror moving section which moves the reflection mirror in a translatory manner in a direction that is substantially perpendicular to the light path of the transmitted illuminative light from the light source, such that when the mirror moving section moves the reflection mirror, the path of the laser beam reflected by the reflection mirror remains substantially parallel to the light path of the transmitted illuminative light;

wherein when the mirror moving section moves the reflection mirror, an incidence angle, at a boundary of the specimen, of the laser beam emitted from the condenser lens is changed, thereby changing a leak-out depth of evanescent light that illuminates the specimen.

42. A total internal reflection fluorescence microscope comprising:

at least one objective lens which takes light from a specimen;

an image pick-up device which picks up an image of the light taken into the objective lens;

an observation optical path via which the light taken into the objective lens is condensed onto the image pick-up device;

a condenser lens, which is disposed in a position facing the objective lens via the specimen, which has a numerical aperture that makes possible total internal reflection illumination, and which guides a transmitted illuminative light, which is emitted by a light source, into the specimen;

a laser oscillation unit which outputs a laser beam;

a laser introduction section which comprises a reflection mirror provided integrally at a lower portion of the condenser lens to reflect the laser beam output from the laser oscillation unit along a path substantially parallel to a light path of the transmitted illuminative light from the light source, so as to introduce the laser beam into a vicinity of an outermost side of the condenser lens; and a mirror moving section which moves the reflection mirror in a translatory manner in a direction that is substantially perpendicular to the light path of the transmitted illuminative light from the light source, such that when the mirror moving section moves the reflection mirror, the path of the laser beam reflected by the reflection mirror remains substantially parallel to the light path of the transmitted illuminative light;

wherein when the mirror moving section moves the reflection mirror, an incidence angle, at a boundary of the specimen, of the laser beam emitted from the condenser lens is changed, thereby changing a leak-out depth of evanescent light that illuminates the specimen.

* * * * *